(12) United States Patent
Hasegawa et al.

(10) Patent No.: US 7,758,704 B2
(45) Date of Patent: Jul. 20, 2010

(54) ENDOSCOPE CLEANING/DISINFECTING APPARATUS

(75) Inventors: Hitoshi Hasegawa, Yokohama (JP); Kojiro Kotani, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 452 days.

(21) Appl. No.: 11/716,249

(22) Filed: Mar. 9, 2007

(65) Prior Publication Data
US 2008/0115814 A1 May 22, 2008

Related U.S. Application Data

(63) Continuation of application No. PCT/JP2006/323038, filed on Nov. 17, 2006.

(51) Int. Cl.
*B08B 3/00* (2006.01)
(52) U.S. Cl. .................. 134/56 R; 134/94.1; 134/201; 600/133
(58) Field of Classification Search ............. 134/56 R, 134/94.1, 201; 600/133
See application file for complete search history.

(56) References Cited

U.S. PATENT DOCUMENTS 6,379,632 B1 * 4/2002 Kinoshita et al. ........... 422/300

6,656,438 B1 12/2003 Kinoshita et al.

FOREIGN PATENT DOCUMENTS

| EP | 1025795 | 8/2000 |
|---|---|---|
| EP | 1025862 | 8/2000 |
| JP | 11-137506 | 5/1999 |
| JP | 2000-287924 | 10/2000 |
| JP | 2000-288069 | 10/2000 |
| JP | 2004-121832 | * 4/2004 |
| JP | 2006-230493 | * 9/2006 |

* cited by examiner

*Primary Examiner*—Michael Barr
*Assistant Examiner*—Jason Heckert
(74) *Attorney, Agent, or Firm*—Scully, Scott, Murphy & Presser, P.C.

(57) ABSTRACT

An endoscope cleaning/disinfecting apparatus of the present invention includes a cleaning tub, a chemical solution tank for storing a germicide, a chemical solution collection pipe, a chemical solution pipe, a feed pipe, a germicide bottle tray which can be drawn from the body of the cleaning/disinfecting apparatus, and a control unit for performing control to prepare the germicide by mixing a basis, a buffering agent, and a diluent. The germicide bottle tray includes a storage part which stores at least a first bottle body out of the first bottle body for storing the basis or a second bottle body for storing the buffering agent, and a detection portion for outputting a detection signal in a state in which the bottle body is stored in the storage part. The control unit performs control based on the detection signal outputted from the detection portion to prepare the germicide.

14 Claims, 14 Drawing Sheets

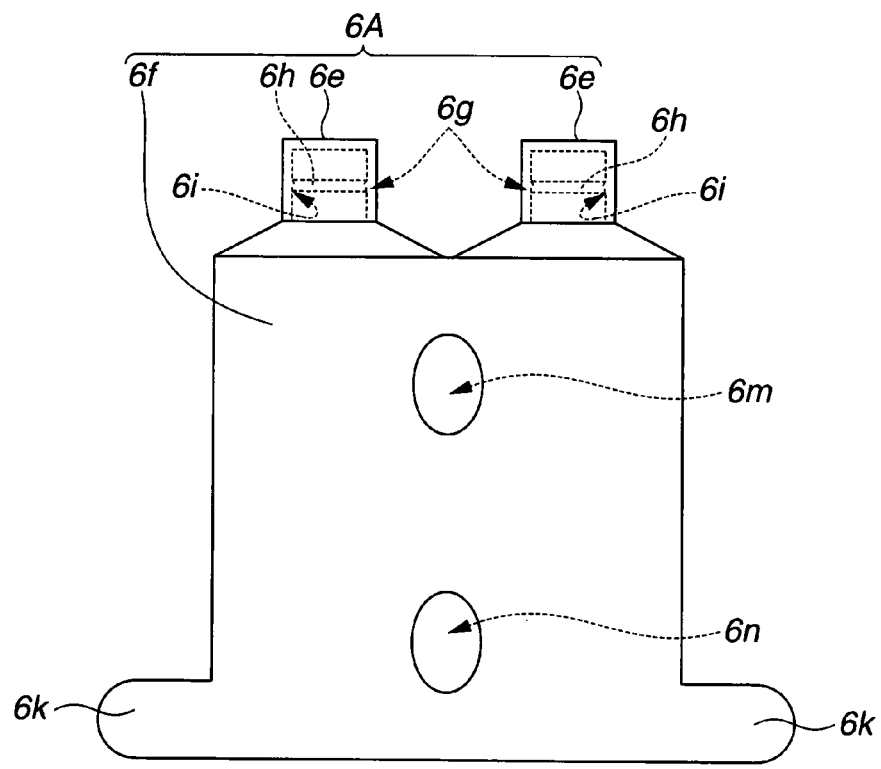
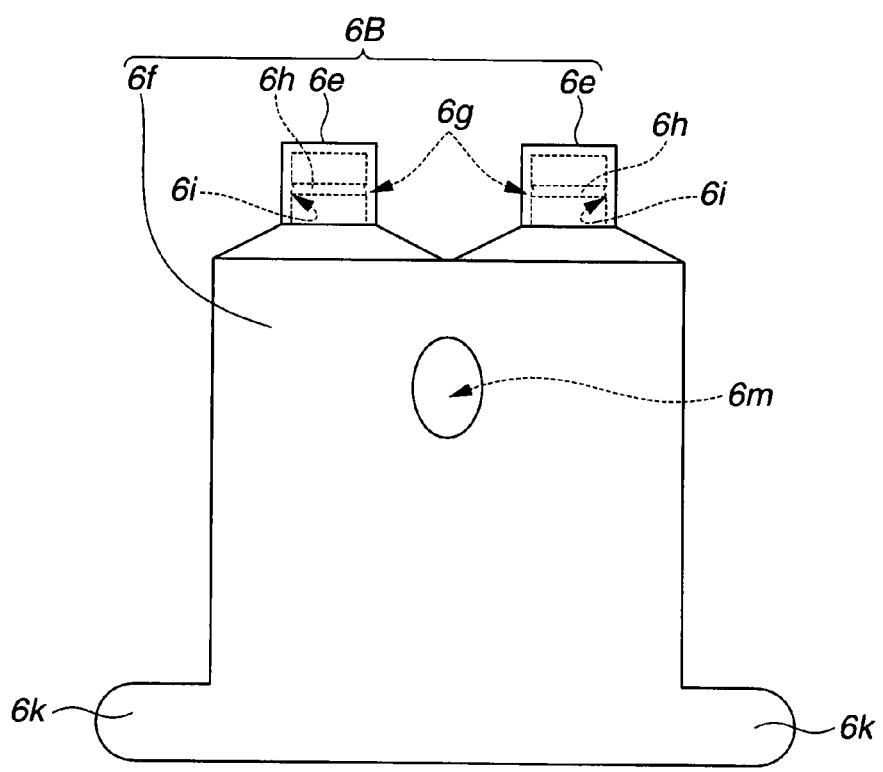

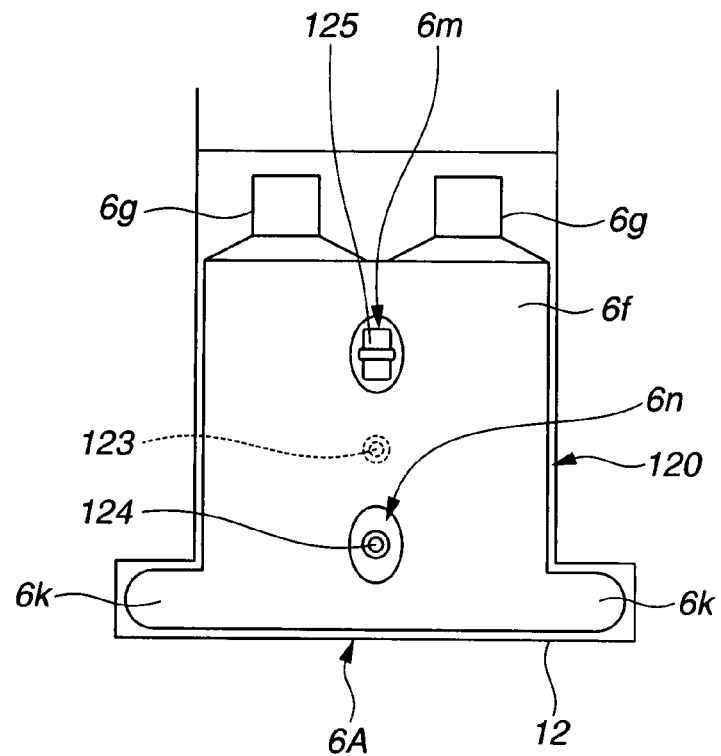
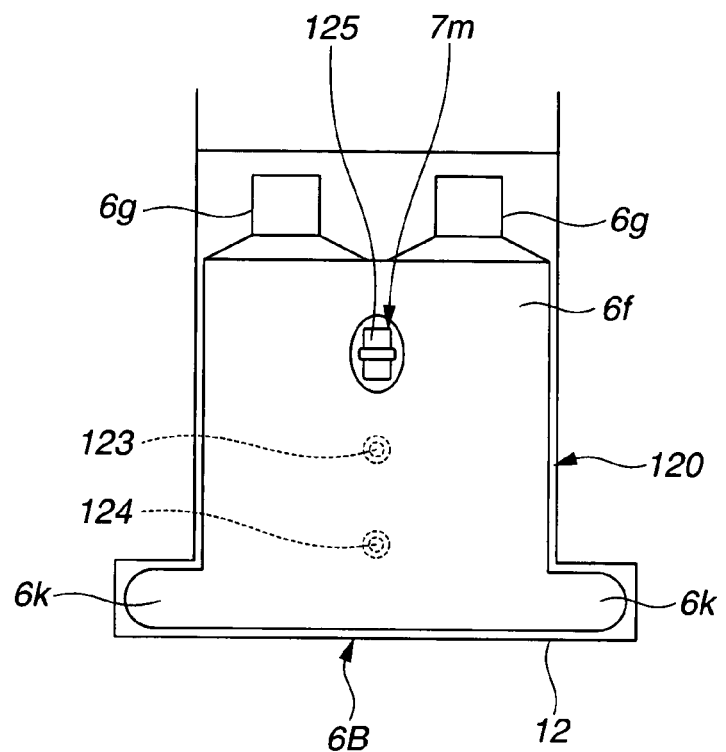

ENDOSCOPE CLEANING/DISINFECTING APPARATUS

CROSS REFERENCE TO RELATED APPLICATION

This application is a continuation application of PCT/JP2006/323038 filed on Nov. 17, 2006 the disclosure of which is incorporated herein by its reference.

BACKGROUND OF THE INVENTION

1. Field of the Invention

The present invention relates to an endoscope cleaning/disinfecting apparatus in which an endoscope stored in a cleaning tub is disinfected by a germicide stored in a chemical solution tank.

2. Description of the Related Art

In recent years, endoscopes have been widely used in a medical field and an industrial field. Endoscopes for a medical field are inserted into body cavities to conduct inspections and treatment, and thus endoscopes used once are always cleaned and disinfected. For example, endoscope cleaning/disinfecting apparatuses are used when endoscopes used once are cleaned and disinfected.

For example, Japanese Patent Laid-Open No. 2006-230493 proposes an endoscope cleaning/disinfecting apparatus in which a channel for quickly feeding a solution in a bottle into a chemical tank is positively formed. In this endoscope cleaning/disinfecting apparatus, as shown in FIG. 15, a germicide bottle tray 12 can be drawn to the front of an apparatus body 2 of the cleaning/disinfecting apparatus. Further, as shown in FIGS. 14 and 15, a bottle body 70 is stored in a storage part 12a of the germicide bottle tray 12. The bottle body 70 is formed by integrally fixing two kinds of bottles, that is, a first bottle 70A and a second bottle 70B with, for example, a tape 79. FIGS. 14 and 15 show the conventional endoscope cleaning/disinfecting apparatus. FIG. 14 is an explanatory drawing of the bottle body formed by combining the first bottle and the second bottle. FIG. 15 is an explanatory drawing of the bottle body and the germicide bottle tray where the bottle body is stored.

A basis obtained by concentrating a germicide is stored in the first bottle 70A and a buffering agent is stored in the second bottle 70B. The bottles 70A and 70B are each made up of a bottle body 71 and a cap 72.

The bottle body 70 formed by combining the first bottle 70A and the second bottle 70B with the tape 79 includes protrusions 73L and 73R that protrude to the left and right, respectively. A hole 74 formed by combining concave portions 74L and 74R is provided substantially at the center of the bottle body 70.

In response to the configuration of the bottles 70A and 70B, the storage part 12a of the germicide bottle tray 12 includes concave portions (not shown) and a convex portion 12c. The concave portions are provided on the front side of the storage part 12a, and the protrusions 73R and 73L provided on the bottle body 70 are respectively disposed on the concave portions. On the other hand, the convex portion 12c protrudes substantially at the center of the storage part 12a so as to be disposed in the hole 74 formed on the bottle body 70.

According to this configuration, when the bottle body 70 formed by combining the first bottle 70A and the second bottle 70B is disposed in the storage part 12a of the germicide bottle tray 12, the protrusions 73L and 73R of the bottle body 70 are disposed in the concave portions provided in the storage part 12a. On the other hand, the convex portion 12c of the storage part 12a is disposed in the hole 74 provided on the bottle body 70. It is thus possible to prevent an inapplicable germicide from being erroneously disposed in the germicide bottle tray 12. In other words, the apparatus is designed such that only a dedicated bottle can be disposed in the storage part 12a of the germicide bottle tray 12.

However, some users request cleaning/disinfecting using an inapplicable germicide.

Even in the case of an inapplicable germicide, when the concentration ratio of a basis and a buffering agent is equal to that of a dedicated type, the basis and the buffering agent of the inapplicable germicide can be respectively stored in the first bottle 70A and the second bottle 70B, so that cleaning and disinfecting can be performed in a similar manner to the dedicated type.

When a germicide is inapplicable and a concentration ratio of the basis and the buffering agent is different from that of the specific type but the total volume of the basis and the buffering agent is equal to that of the dedicated type, cleaning and disinfecting can be performed in a similar manner to the dedicated type by, for example, changing the shapes of the bottles as shown in FIG. 16. To be specific, as shown in FIG. 16 illustrating an example of another way to combine two bottles making up the bottle body, the two kinds of bottles are formed in consideration of the volumes of the chemical solutions such that the bottle body 70 is formed by combining a first bottle 70C for storing the basis and the second bottle 70D for storing the buffering agent.

However, in the presence of a plurality of kinds of germicide of various concentration types, it is seldom that a concentration rate of a basis and a buffering agent is equal to that of the dedicated type or a concentration rate of a basis and a buffering agent is different from that of the dedicated type but the total volume of the basis and the buffering agent is equal to that of the dedicated type.

The present invention is designed in view of the foregoing circumstances. An object of the present invention is to provide an endoscope cleaning/disinfecting apparatus enabling cleaning/disinfecting with germicides of various concentration types without greatly modifying the body of the cleaning/disinfecting apparatus.

SUMMARY OF THE INVENTION

An endoscope cleaning/disinfecting apparatus of the present invention includes a cleaning tub which is disposed on the body of the cleaning/disinfecting apparatus and stores an endoscope, a chemical solution tank for storing a germicide obtained by mixing a basis, a buffering agent, and a diluent, a chemical solution pipe for supplying the germicide of the chemical solution tank into the cleaning tub, a feed pipe for supplying tap water into the cleaning tub, and a chemical solution collection pipe for connecting the cleaning tub and the chemical solution tank, the endoscope cleaning/disinfecting apparatus cleaning and disinfecting the endoscope stored in the cleaning tub with the germicide stored in the chemical solution tank, wherein the body of the cleaning/disinfecting apparatus includes a germicide bottle tray and a control unit, the germicide bottle tray including a storage part which stores at least a first bottle body out of the first bottle body for storing the basis and a second bottle body for storing the buffering agent, and a detection portion for outputting a detection signal in a state in which the bottle body is stored in the storage part, the germicide bottle tray being freely drawn from the body of the cleaning/disinfecting apparatus, the germicide bottle tray guiding the mouth of the bottle body to a mouth placement part provided on one end of a chemical solution supply pipe having the other end communicating with the chemical solution tank, the control unit performing control, based on the detection signal outputted from the detection portion, so that the germicide is prepared by mixing the basis, the buffering agent, and the diluent.

Therefore, under the control of the control unit, the germicide is prepared by feeding the basis of the first bottle body, the buffering agent of the second bottle body, and tap water serving as a diluent into the chemical solution tank.

BRIEF DESCRIPTION OF THE DRAWINGS

FIGS. 1 to 11 show an embodiment of the present invention;

FIG. 1 is a perspective view illustrating an endoscope cleaning/disinfecting apparatus;

FIG. 2 is a block diagram illustrating the endoscope cleaning/disinfecting apparatus;

FIG. 3 is a plan view illustrating the main operation panel of the endoscope cleaning/disinfecting apparatus;

FIG. 4 is a plan view illustrating the sub operation panel of the endoscope cleaning/disinfecting apparatus;

FIG. 5 illustrates a structural example of a basis bottle;

FIG. 6 illustrates a structural example of a buffering agent bottle;

FIG. 7 illustrates the configuration of a cassette tray;

FIG. 8 is a flowchart illustrating an example of a germicide preparation program;

FIG. 9 illustrates a state in which the basis bottle is stored in the storage part of the cassette tray;

FIG. 10 illustrates a state in which the buffering agent bottle is stored in the storage part of the cassette tray;

FIG. 11 illustrates a state in which the chemical solution of the basis bottle is supplied into a chemical solution tank;

FIG. 12 illustrates a fluid volume detection unit;

FIG. 13 is a flowchart for explaining the another germicide preparation program;

FIG. 14 illustrates a bottle body formed by combining a first bottle and a second bottle;

FIG. 15 illustrates the bottle body and a germicide bottle tray for storing the bottle body.

DETAILED DESCRIPTION OF THE PREFERRED EMBODIMENT(S)

Embodiments of the present invention will now be described below with reference to the accompanying drawings.

Referring to FIGS. 1 to 11, the following will describe an embodiment of the present invention.

Figure 1:
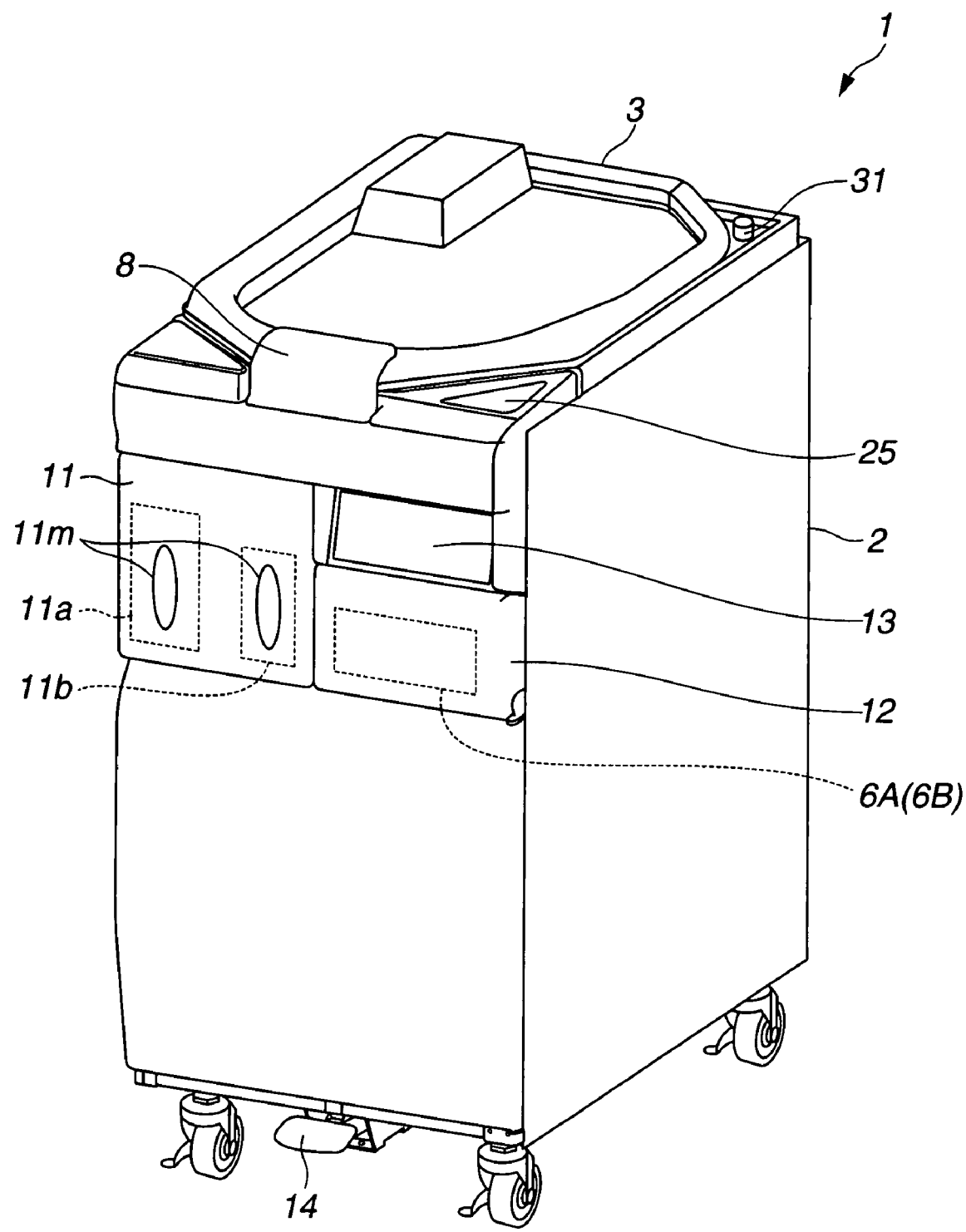

An endoscope cleaning/disinfecting apparatus 1 shown in FIG. 1 is an apparatus for cleaning and disinfecting a used endoscope (not shown). The main part of the endoscope cleaning/disinfecting apparatus 1 includes a body 2 of the cleaning/disinfecting apparatus (hereinafter, will be abbreviated to the apparatus body) and a top cover 3 which is a lid connected on the apparatus body 2 so as to open and close via, for example, a hinge (not shown).

The apparatus body 2 and the top cover 3 are opposed to each other, and the top cover 3 is integrally fixed to the apparatus body 2 via, for example, a latch 8.

In FIG. 1, a detergent/alcohol tray 11 is disposed on, a front face of the apparatus body 2 to which an operator comes close (hereinafter, will be referred to as the front), for example, the upper left of the front. The detergent/alcohol tray 11 can be drawn to the front of the apparatus body 2.

The detergent/alcohol tray 11 stores a detergent tank 11a and an alcohol tank 11b. The detergent tank 11a stores a detergent which is a solution used for cleaning an endoscope. The alcohol tank 11b stores an alcohol used for drying an endoscope after cleaning and disinfecting. Since the detergent/alcohol tray 11 can be drawn, the tanks 11a and 11b can be refilled with predetermined liquids.

Reference numeral 11m denotes viewing windows which correspond to the positions of the tanks 11a and 11b stored in the detergent/alcohol tray 11. To be specific, the user can visually confirm, through the two viewing windows 11m, the remaining amounts of a detergent and alcohol stored in the tanks 11a and 11b. The detergent is a concentrated detergent to be diluted to a predetermined concentration with tap water having been filtered through a feed filter (reference numeral 17 in FIG. 2). The cleaning solution of the present embodiment is a mixed solution of the detergent and the tap water.

Meanwhile, at the front of the apparatus body 2, for example, on the upper right of the front, a germicide bottle tray 12 is disposed which can be drawn to the front of the apparatus body 2.

Figure 14:
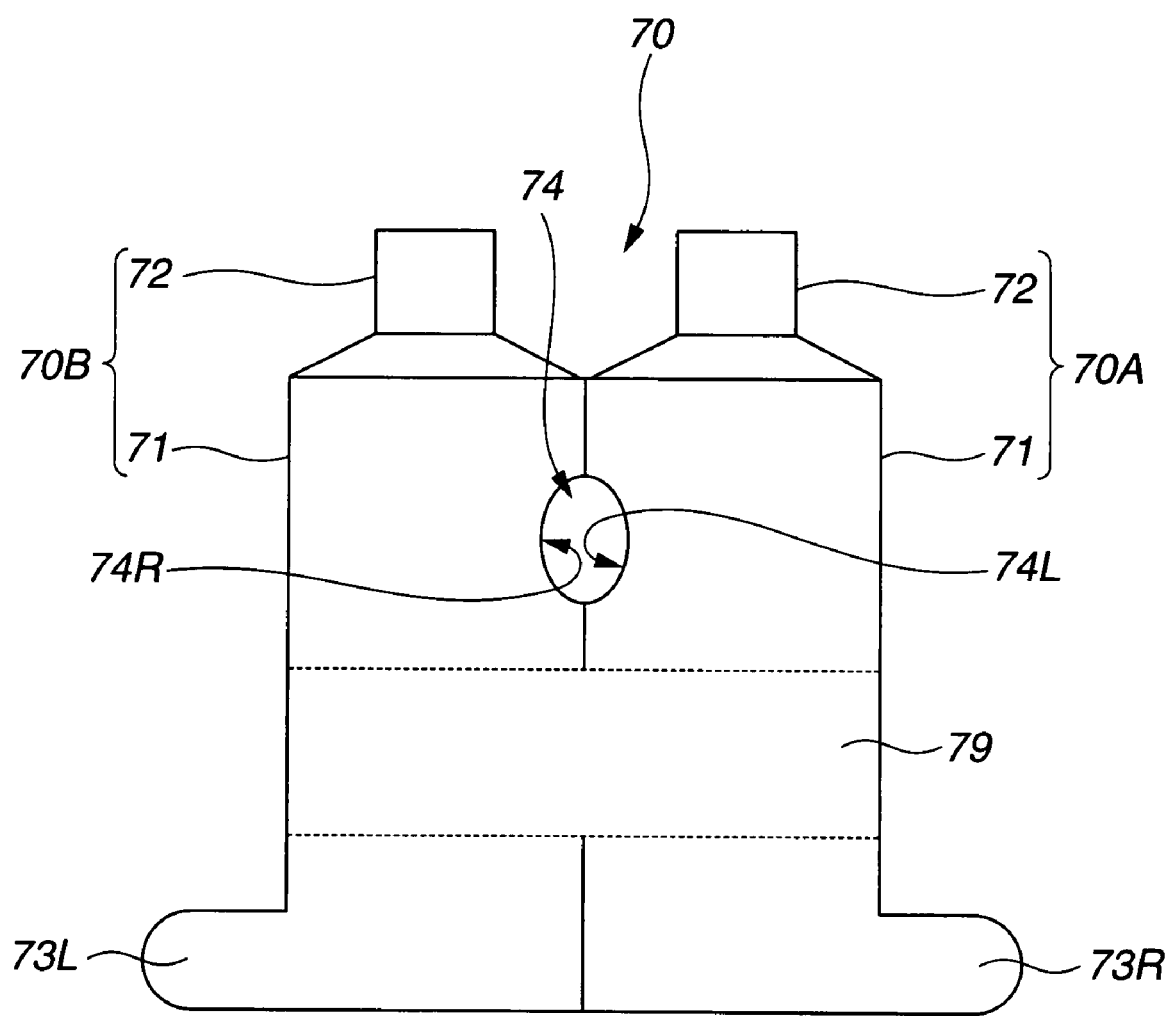
FIGS. 14 and 15 show a conventional endoscope cleaning/disinfecting apparatus.
Figure 15:
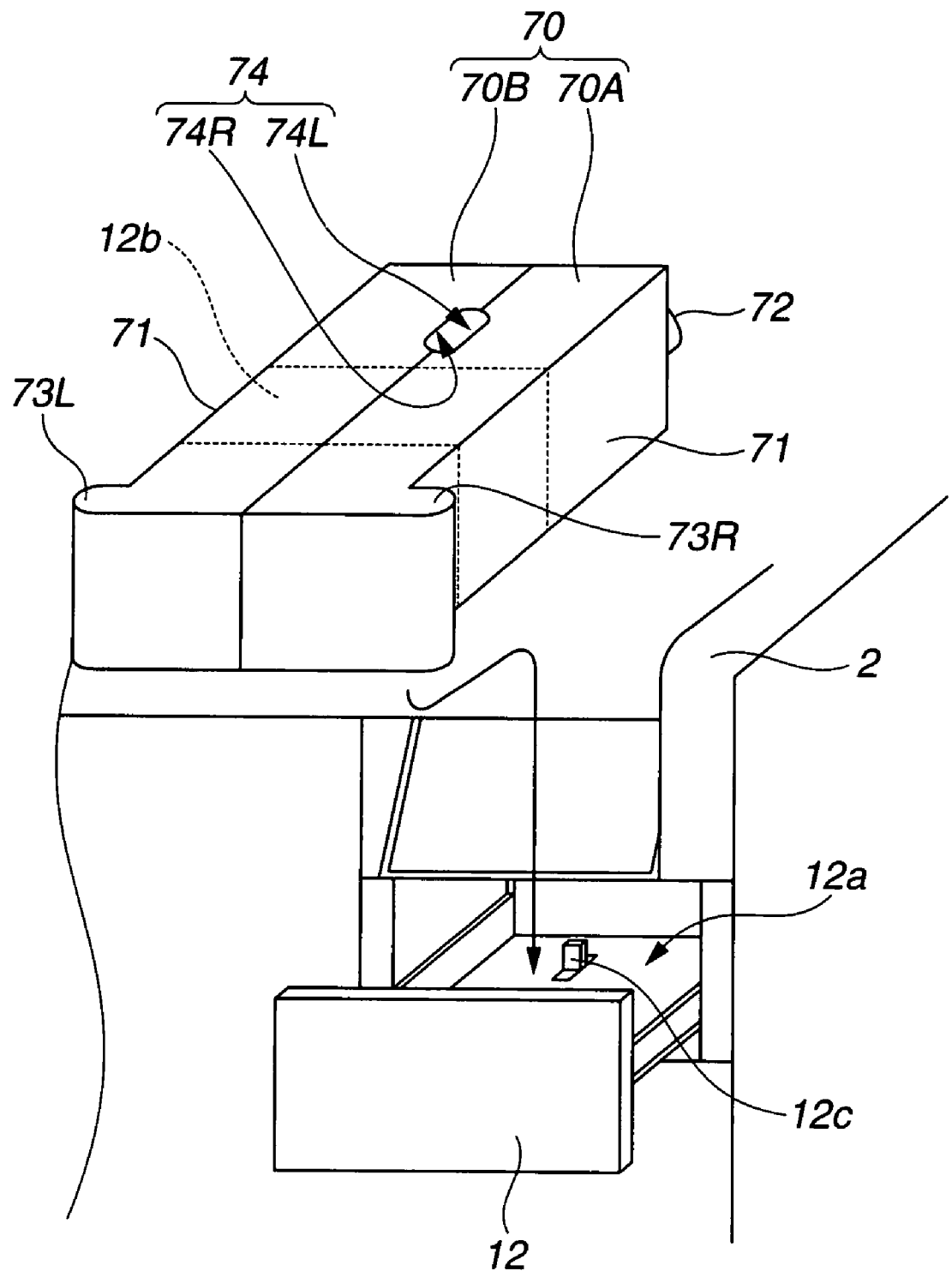
Figure 16:
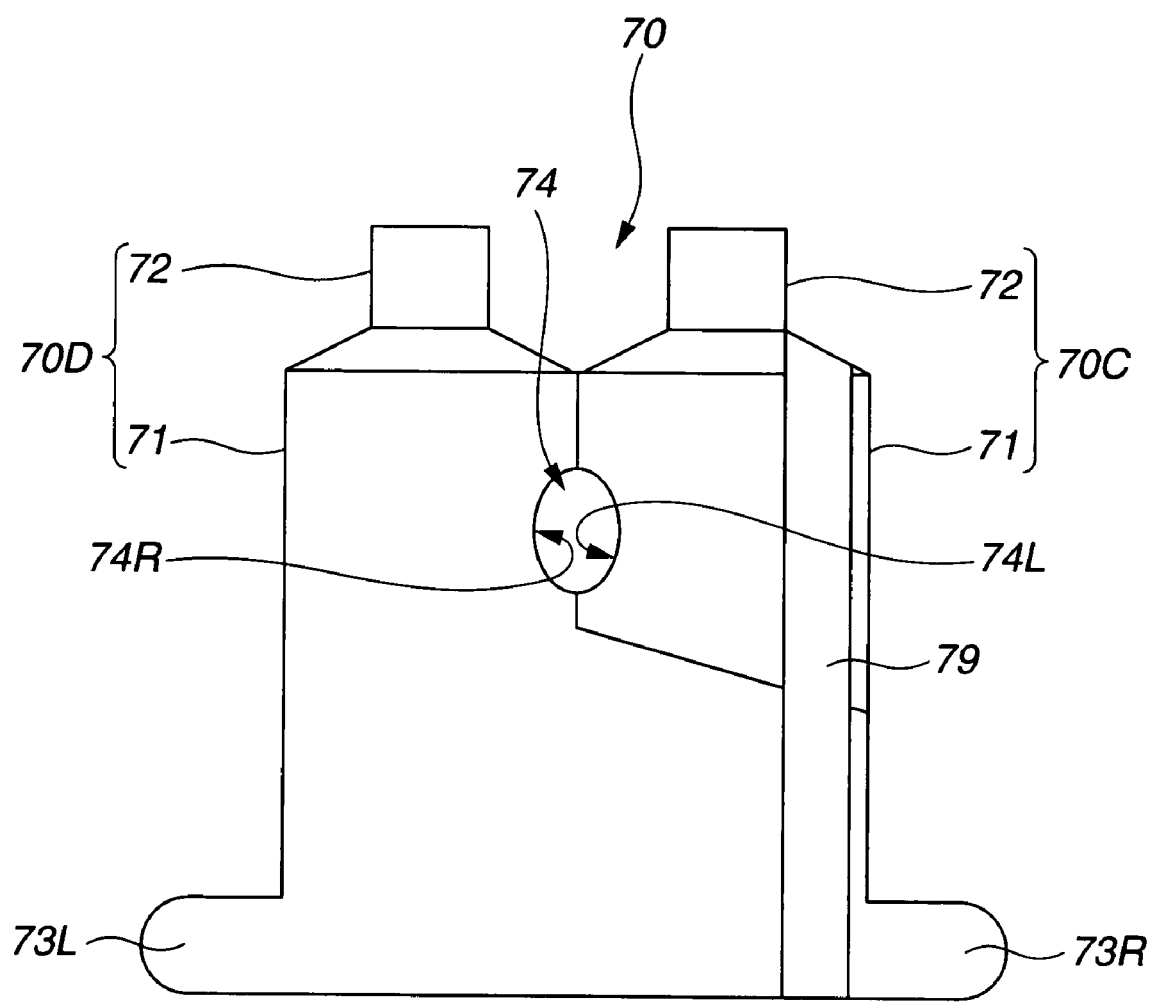
FIG. 16 illustrates an example of another way to combine the two bottles making up the bottle body.

The germicide bottle tray 12 can store a bottle 6 which is shaped like the bottle body 70 formed by combining the bottles 70A and 70B shown in FIGS. 14 and 15. In the present embodiment, the bottle 6 includes two kinds of bottles, that is a first bottle (will be referred to as a basis bottle) 6A for storing a basis such as peracetic acid therein and a second bottle (will be referred to as a buffering agent bottle) 6B for storing a buffering agent therein. Since the germicide bottle tray 12 can be drawn from the apparatus body 2, the basis bottle 6A and the buffering bottle 6B can be replaced with each other. In the present embodiment, a mixed solution of the basis, the buffering agent, and the tap water is a germicide.

Further, at the front of the apparatus body 2, a sub operation panel 13 is disposed on the germicide bottle tray 12. The sub operation panel 13 displays a cleaning/disinfecting time and includes instruction buttons or the like for heating a germicide.

Moreover, on the top surface of the apparatus body 2 and, for example, at the front where an operator comes close, a main operation panel 25 is disposed. The main operation panel 25 includes setting switches such as switches for starting cleaning/disinfecting of the apparatus body 2 and switches for selecting cleaning/disinfecting modes.

Further, on the top surface of the apparatus body 2 and on the opposite side from the front where an operator comes close, a water hose port 31 is disposed. A hose connected to a water tap (reference numeral 5 of FIG. 2) to feed tap water to the apparatus body 2 is connected to the water hose port 31. A mesh filter for filtering tap water may be disposed on the water hose port 31.

Moreover, a pedal 14 is disposed on the lower part of the front of the apparatus body 2 in FIG. 1. The pedal 14 opens the top cover 3 closed on the top surface of the apparatus body 2, to the above of the apparatus body 2 in response to the pedaling operation of an operator.

When the top cover 3 is opened, a cleaning tub (reference numeral 4 in FIG. 2) appears which is disposed substantially at the center of the top surface of the apparatus body 2. The cleaning tub 4 can store an endoscope.

Figure 2:
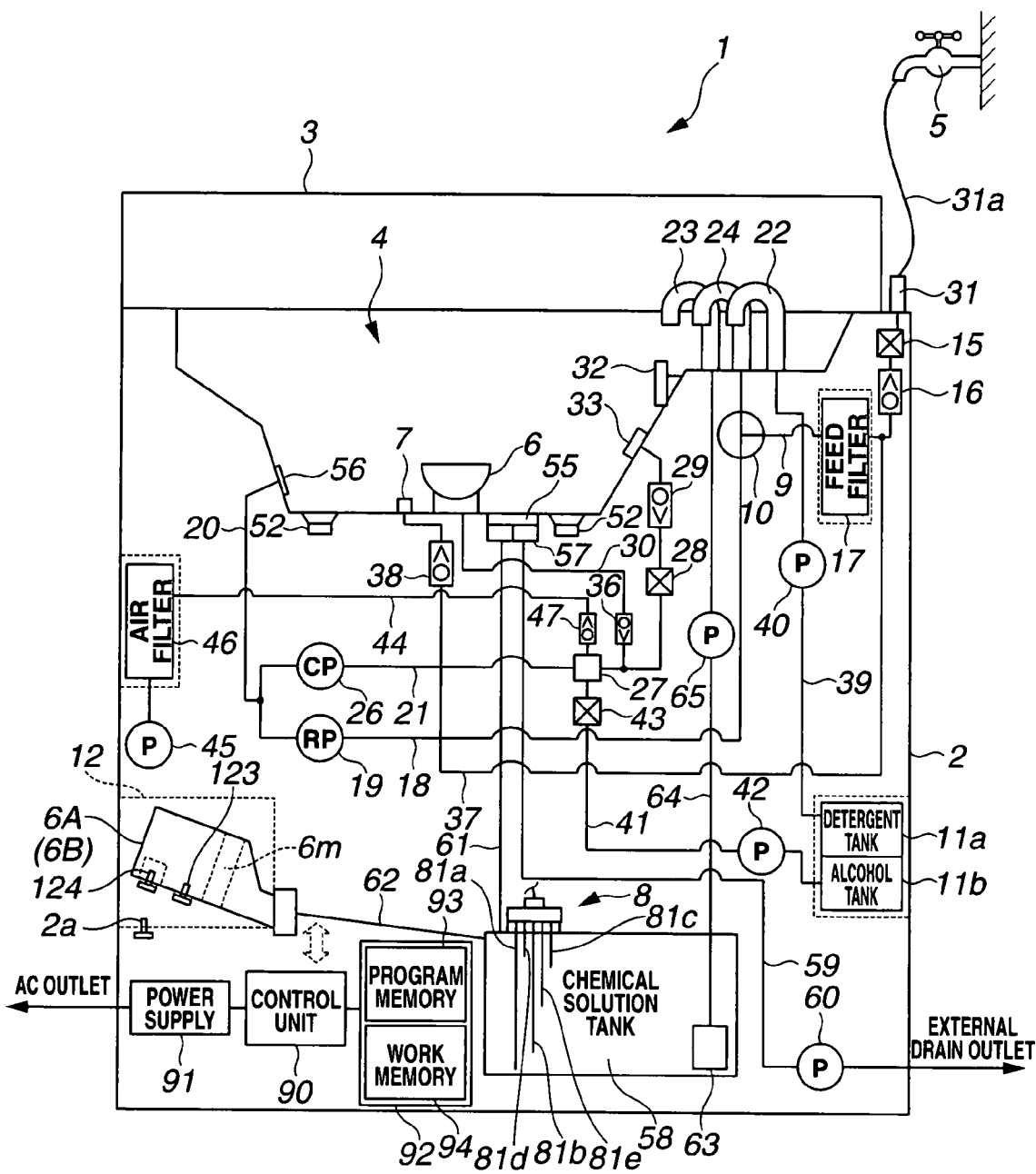

As shown in FIG. 2, a drain outlet 55 is disposed on the bottom surface of the cleaning tub 4. The drain outlet 55 is provided to drain a cleaning solution, water, alcohol, a germicide or the like supplied into the tub.

On a given position on a side of the cleaning tub 4, a circulating port 56 is disposed to circulate a cleaning solution, water, a germicide or the like supplied into the tub. Water or the like drained from the circulating port 56 is supplied to a feed nozzle 24 (described later). A mesh filter for filtering a cleaning solution or the like may be disposed on the circulating port 56.

On a side of the cleaning tub 4, a water level sensor 32 with a cover is disposed to detect the water level of a cleaning solution, water, a germicide or the like supplied into the cleaning tub 4.

A feed pipe disinfection port 7 or the like is provided in the cleaning tub 4. The feed pipe disinfection port 7 supplies, as will be described later, a germicide to pipes in the apparatus through a cleaning tube to disinfect feed pipes.

A detergent nozzle 22, a germicide nozzle 23, and the feed nozzle 24 are disposed on the top surface of the cleaning tub 4. The detergent nozzle 22 supplies, into the tub, a cleaning solution in the detergent tank 11*a* through a pump 40 (described later). The germicide nozzle 23 supplies, into the tub, a germicide in a chemical solution tank 58. The feed nozzle 24 supplies, into the tub, tap water or a cleaning solution, water, a germicide and so on which have been sucked from the circulating port 56.

Figure 3:
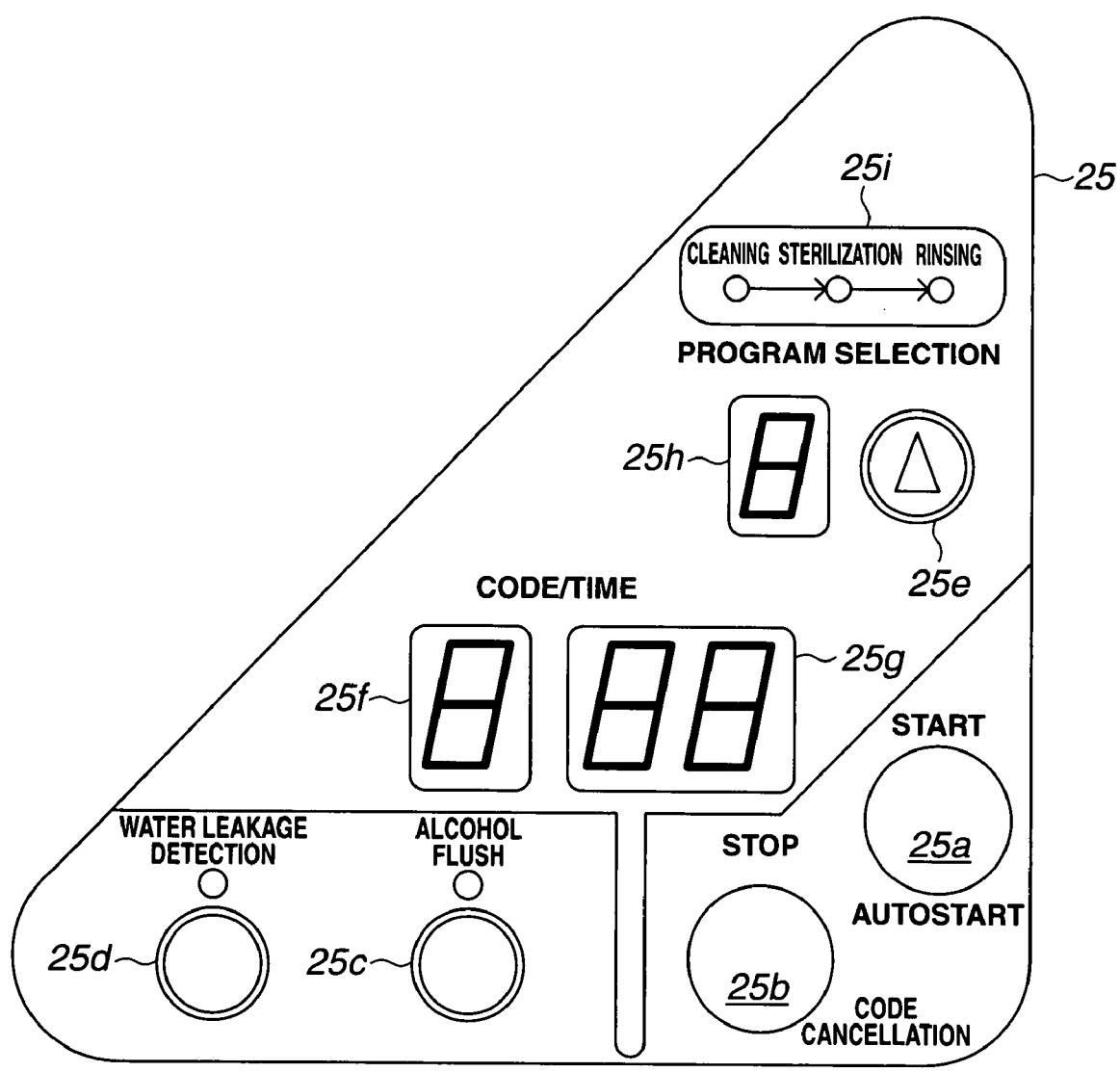

Referring to FIG. 3, the main operation panel 25 will now be described below.

As shown in FIG. 3, the main operation panel 25 includes a start button 25*a* for driving the endoscope cleaning/disinfecting apparatus 1 and a stop button 25*b* for stopping the endoscope cleaning/disinfecting apparatus 1. The buttons 25*a* and 25*b* are disposed on the lower right of FIG. 3. Further, from the left of the stop button 25*b*, a button 25*c* for alcohol flush and a button 25*d* for detecting water leakage of the endoscope are disposed on the main operation panel 25. Above the buttons 25*c* and 25*d*, illuminants such as LEDs are disposed to be illuminated so as to distinguish driving between alcohol flush and detection of water leakage.

A code display part 25*f* and a time display part 25*g* for displaying the driving time of the apparatus are disposed substantially at the center of the main operation panel 25. A program selection button 25*e* and a program display part 25*h* are disposed on the upper right of the display parts 25*f* and 25*g* of the main operation panel 25. The program display part 25*h* displays a program number in response to an operation of the program selection button 25*e*. Further, above the program selection button 25*e* and the program display part 25*h*, a process display part 25*i* is disposed which enables the user to visually confirm a cleaning process, a disinfecting process, and a rinsing process during the processes through illuminants such as LEDs.

Figure 4:
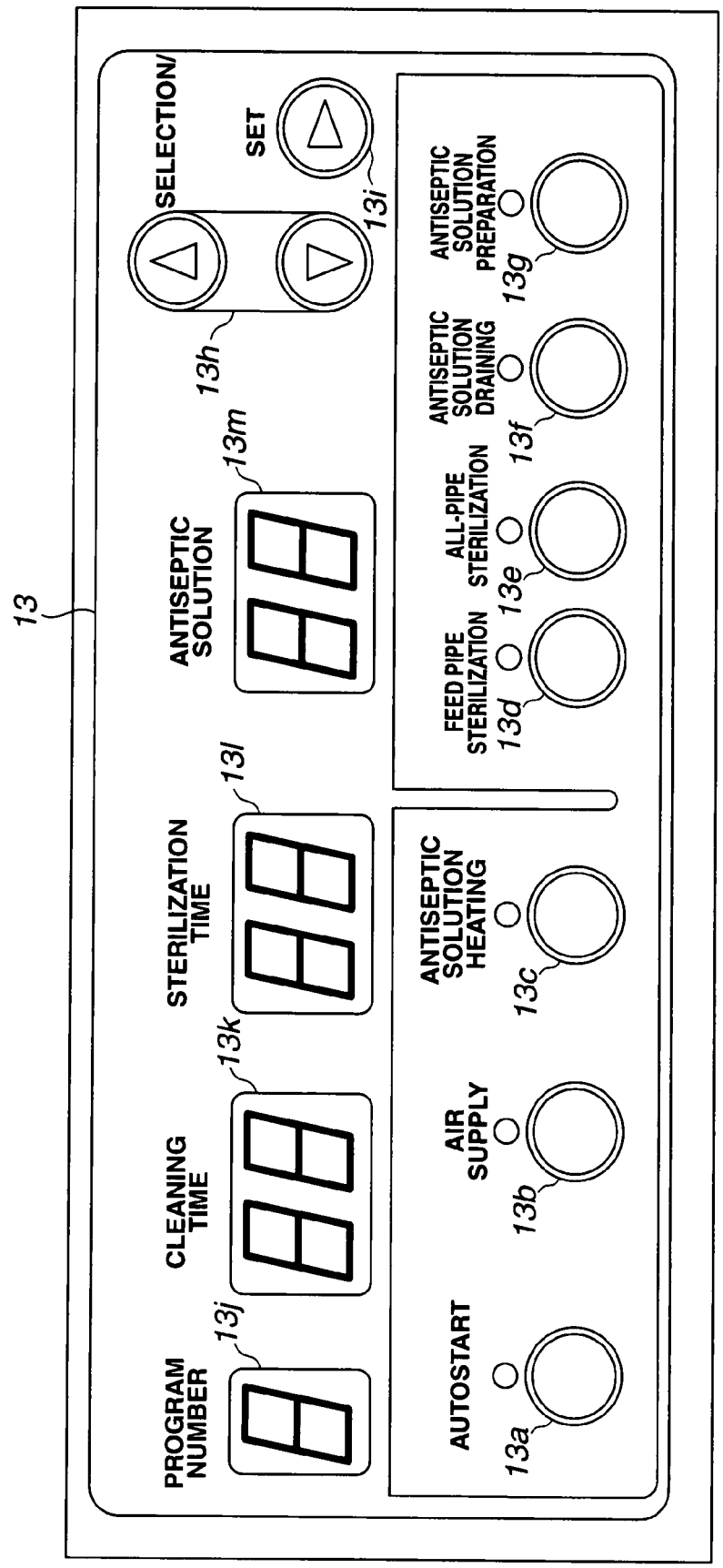

Referring to FIG. 4, the sub operation panel 13 will now be described below.

As shown in FIG. 4, the sub operation panel 13 includes a plurality of operation buttons which are disposed on the lower part in FIG. 4. The plurality of operation buttons are, from the left, an autostart button 13*a*, an air supply button 13*b*, a germicide heating button 13*c*, a feed pipe disinfection button 13*d*, an all-pipe disinfection button 13*e*, a germicide draining button 13*f*, and a germicide preparation button 13*g*.

Above these buttons, a program number display part 13*j*, a cleaning time display part 13*k*, a disinfecting time display part 13*l*, and a germicide use times display part 13*m* are disposed from the left. On the right of these display parts, a selection setting button 13*h* and a set button 13*i* are disposed.

Generally in the endoscope cleaning/disinfecting apparatus 1 of the present embodiment, when a used endoscope is cleaned/disinfected by an operation of the main operation panel 25, the operation is performed by a predetermined cleaning/disinfecting program in response to the operations of the program selection button 25*e* and the start button 25*a*. The cleaning/disinfecting program enables the user to arbitrarily set a cleaning time, a disinfecting time, and so on by means of the buttons of the sub operation panel 13.

Referring to FIG. 2 again, the internal configuration of the endoscope cleaning/disinfecting apparatus 1 will be described below.

As shown in FIG. 2, one end of a water hose 31*a* is connected to the water hose port 31 of the endoscope cleaning/disinfecting apparatus 1 and the other end of the water hose 31*a* is connected to the water tap 5.

The water hose port 31 is connected to one end of a feed pipe 9. The other end of the feed pipe 9 is connected to a three-way solenoid valve 10. A water feed solenoid valve 15, a check valve 16, and a feed filter 17 are interposed on the pipe in this order from the side of the water hose port 31.

The three-way solenoid valve 10 is connected to one end of a liquid pipe 18 and switches the connection of the feed pipe 9 and the connection of the liquid pipe 18 to the feed nozzle 24 by means of the internal valve. In other words, the feed nozzle 24 is connected to one of the feed pipe 9 and the liquid pipe 18 by the switching operation of the three-way solenoid valve 10. The other end of the liquid pipe 18 is connected to a liquid pump 19.

One end of a circulating pipe 20 is connected to the circulating port 56 disposed in the cleaning tub 4. The other end of the circulating pipe 20 is divided into two so as to connect to the other end of the liquid pipe 18 via the liquid pump 19 and one end of a channel pipe 21 via a channel pump 26.

The other end of the channel pipe 21 is connected to each air water supply/forceps port 33. In FIG. 2, only one of the air water supply/forceps ports 33 is illustrated.

In the mid-course of channel pipe 21, a channel block 27, a CH (channel) solenoid and check valves 28 and 29 are interposed in this order from the side of the channel pump 26.

One end of a disinfection pipe 37 is connected to the feed pipe disinfection port 7 installed in the cleaning tub 4. The other end of the disinfection pipe 37 is connected to the feed pipe 9 between the feed filter 17 and the check valve 16. A check valve 38 is interposed on the disinfection pipe 37 on the side of the feed pipe disinfection port 7.

One end of a detergent pipe 39 is connected to the detergent nozzle 22 and the other end of the detergent pipe 39 is connected to the detergent tank 11*a*. The detergent feed pump 40 is interposed in mid-course of the detergent pipe 39.

One end of an alcohol pipe 41 is connected to the alcohol tank 11*b* and the other end of the alcohol pipe 41 is connected to the channel block 27 so as to communicate with the channel pipe 21 in a predetermined state. An alcohol supply pump 42 is interposed on the alcohol pipe 41 on the side of the alcohol tank 11*b* and a solenoid valve 43 is interposed on the alcohol pipe 41 on the side of the channel block 27.

One end of an air pipe 44 for supplying air from an air pump 45 is connected to the channel block 27 so as to communicate with the channel pipe 21 in a predetermined state. The other end of the air pipe 44 is connected to the air pump 45 via an air filter 46. A check valve 47 is interposed on the air pipe 44 on the side of the channel block 27.

A change-over valve 57 is disposed in the drain outlet 55 of the cleaning tub 4. By the switching operation of the change-over valve 57, a cleaning solution in the tank can be drained to the outside of the apparatus or a germicide in the tank can be collected to the chemical solution tank 58. One end of a drain pipe 59 and one end of a chemical solution collecting pipe 61 are connected to the change-over valve 57. The other end of the drain pipe 59 is connected to a drain hose via a drain pump 60. The drain hose is connected to an external drain outlet. The other end of the chemical solution collecting pipe 61 is connected to the chemical solution tank 58.

One end of a chemical solution supply pipe 62 is connected to the chemical solution tank 58. The other end of the chemical solution supply pipe 62 is connected to the germicide bottle tray 12 in a predetermined state. The germicide bottle tray 12 in which one of the bottles 6A and 6B is stored is set in the apparatus body 2, so that a chemical solution in the basis bottle 6A or a chemical solution in the buffering agent bottle 6B is supplied into the chemical solution tank 58 through the chemical solution supply pipe 62.

Reference numeral 123 denotes a bottle detection switch making up a detection part. The bottle detection switch 123 detects whether one of the bottles 6A and 6B is stored or not in the germicide bottle tray 12. Reference numeral 124 denotes a bottle identification switch making up the detection part. For example, in a state in which the basis bottle 6A is stored in the germicide bottle tray 12, the bottle identification switch 124 does not output a detection signal. Only when the buffering agent bottle 6B is stored, the bottle identification switch 124 outputs the detection signal. The switches 123 and 124 are, for example, mechanical switches which can be protruded and depressed. The detection signal is outputted when the switches change from a protruded state to a depressed state.

Reference numeral 2a denotes a lock switch serving as a tray operation switching part which switches the germicide bottle tray 12 between a drawing state and an immovable state. The lock switch 2a can switch from a lock state to a free state and switch from the free state to the lock state under the control of a control unit 90 (described later). Further, when the germicide bottle tray 12 is pressed back into the apparatus body 2 in a predetermined state, the lock switch 2a is changed from the free state to the lock state by the urging force of a urging member (not shown). The lock switch 2a outputs a lock signal to the control unit 90 in the lock state. The detection signals from the switches 123 and 124 are also outputted to the control unit 90.

One end of a chemical solution pipe 64 is disposed in the chemical solution tank 58. A suction filter 63 is provided on the one end of the chemical solution pipe 64. The other end of the chemical solution pipe 64 is connected to the germicide nozzle 23 via a chemical solution pump 65.

On the top surface of the cleaning tub 4, a fluid volume detection unit 80 is disposed. The fluid volume detection unit 80 detects the volume of a liquid stored in the chemical solution tank 58. The fluid volume detection unit 80 includes a plurality of electrode sensors 81a, 81b, 81c, 81d and 81e having different lengths.

The first electrode sensor 81a is a ground electrode. The second electrode sensor 81b is a basis level detection sensor and is an electrode for detecting the volume of a chemical solution supplied from the basis bottle 6A to the chemical solution tank 58. The third electrode sensor 81c is a diluent level detection sensor and is an electrode for detecting a liquid volume when a chemical solution in the basis bottle 6A is diluted with water serving as a dilute solution and the water reaches a predetermined volume. The fourth electrode sensor 81d is a germicide level detection sensor and an electrode for detecting the volume of a germicide prepared by mixing the chemical solution of the basis bottle 6A, water serving as a diluent, and the chemical solution of the buffering agent bottle 6B. The fifth electrode sensor 81e is an electrode for detecting the minimum volume for supplying a germicide into the cleaning tub 4 in a cleaning/disinfecting state.

The control unit 90 is electrically connected to a power supply 91 fed with power from an external AC outlet. The control unit 90 controls the driving of the pumps, the solenoid valves, the switches and so on mentioned above based on the signals supplied from the main operation panel 25 and the sub operation panel 13 which are shown in FIGS. 3 and 4.

A storage device 92 includes a program memory 93 and a work memory 94. The program memory 93 stores various programs. The work memory 94 stores the operating states of the pumps, the solenoid valves, and the switches which are operated based on the programs. The control unit 90 and the storage device 92 make up a controller.

The control unit 90 also performs control and so on to drive and stop a heater (not shown) based on a detection result from a temperature sensor (not shown) such that a germicide is kept at a predetermined temperature.

Figure 7:
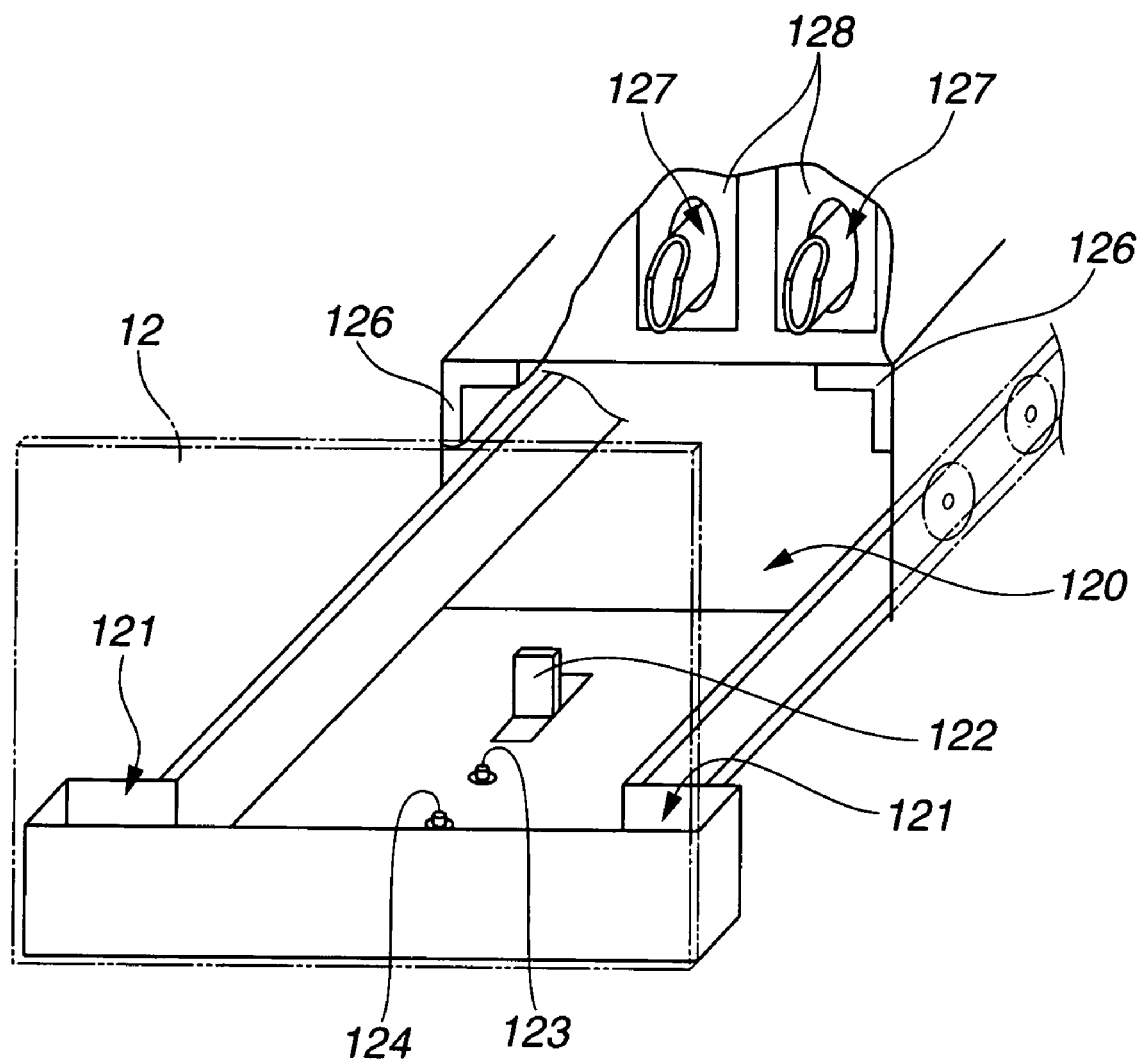

Referring to FIGS. 5 to 7, a structural example of the bottles and the cassette tray will now be described below.

FIG. 5 shows the basis bottle 6A including a box-like bottle body 6f, in which a chemical solution is stored, and cylindrical caps 6e. The shape of the basis bottle 6A is identical to that of the bottle body 70 formed by integrally fixing the first bottle 70A and second bottle 70B with the tape 79 shown in FIGS. 14 and 15.

The bottle body 6f includes mouths 6g substantially shaped like cylinders with openings from which a stored chemical solution is drained. The caps 6e can be attached to the mouths 6g. In the mouth 6g, a closed portion 6h for closing the opening is provided. The outer periphery of the closed portion 6h is configured as a thin portion 6i which is provided over the inner surface of the mouth 6g.

Further, a pair of protrusions 6k are provided on the side wall undersurface of the bottle body 6f in the figure. The bottle body 6f further includes a first through hole 6m and a second through hole 6n. The first through hole 6m is a relief hole where a convex portion 125 (described later) of FIG. 7 is disposed, and the second through hole 6n is a relief hole acting as an identification portion for identifying whether the basis bottle 6A or the buffering agent bottle 6B is stored. The bottle identification switch (hereinafter, will be referred to as a second detection portion) 124 is disposed in the second through hole 6n.

Although one kind of chemical solution is stored in the basis bottle 6A of the present embodiment, the basis bottle 6A has the two mouths 6g.

FIG. 6 shows the buffering agent bottle 6B. A bottle body 6f making up the buffering agent bottle 6B only includes a first through hole 6m in which the convex portion 125 is disposed. The other configurations of the buffering agent bottle 6B are similar to those of the basis bottle 6A and the shape of the buffering agent bottle 6B is also identical to that of the basis bottle 6A.

As shown in FIG. 7, the germicide bottle tray 12 includes a storage part 120. The storage part 120 stores the bottles 6A and 6B each of which includes the pair of protrusions 6k. Thus the storage part 120 includes an engaging part 121 corresponding to the pair of protrusions 6k included in the bottles 6A and 6B.

On an undersurface 122 of the storage part 120, the convex portion 125 is provided in addition to the bottle detection switch (hereinafter, will be referred to as a first detection portion) 123 and the second detection portion 124. The convex portion 125 is a portion for mechanically deciding whether the bottle matches with the storage part 120.

With this configuration, when the buffering agent bottle 6B is disposed in the storage part 120, the first detection portion 123 and the second detection portion 124 are turned on by the bottle body 6f. Thus a first detection signal is outputted from the first detection portion 123 to the control unit 90 and a second detection signal is outputted from the second detection portion 124 to the control unit 90.

On the other hand, when the basis bottle 6A is disposed in the storage part 120, the second detection portion 124 is disposed in the second through hole 6n of the bottle body 6f of the basis bottle 6A, so that only the first detection portion 123 is turned on by the bottle body 6f. Therefore, when the basis bottle 6A is disposed in the storage part 120, only the first detection signal is outputted from the first detection portion 123 to the control unit 90.

Reference numeral 126 in FIG. 7 denotes guide members. When the germicide bottle tray 12 is pressed back into the apparatus body 2 while one of the bottles 6A and 6B is stored in the storage part 120, the upper corners of the bottles 6A and 6B stored in the storage part 120 are brought into contact with the guide members 126. Thus as the germicide bottle tray 12 moves, the mouths 6g of the bottles 6A and 6B are guided to mouth placement parts 128 including closed-portion opening portions 127. In a state in which the germicide bottle tray 12 is pressed back into the apparatus body 2, the closed-portion opening portions 127 break through the thin portions 6i of the closed portions 6h. Thus chemical solutions in the bottles 6A and 6B are drained from the bottle bodies 6f and supplied into the chemical solution tank 58. The closed-portion opening portion 127 makes up the other end of the chemical solution supply pipe 62.

The operation of the endoscope cleaning/disinfecting apparatus 1 configured thus will now be described below.

When it is decided that a germicide is used for cleaning/disinfecting of an endoscope a predetermined number of times, the control unit 90 of the endoscope cleaning/disinfecting apparatus 1 performs control so that an instruction to replace the germicide is displayed on the display part on the main operation panel 25 or the sub operation panel 13. A user who confirms the instruction to replace the germicide replaces the germicide.

The replacement of a germicide includes two processes: a germicide draining process and a germicide preparation process.

First, the user operates the germicide draining button 13f provided on the sub operation panel 13 of the endoscope cleaning/disinfecting apparatus 1. Next, an instruction signal is outputted from the germicide draining button 13f to the control unit 90. The control unit 90 having received the instruction signal starts control based on a germicide draining program stored in the program memory 93.

To be specific, the chemical solution pump 65, the changeover valve 57, and the drain pump 60 are driven under the control of the control unit 90, and a germicide in the chemical solution tank 58 is drained from the external drain outlet through the chemical solution pipe 64, the germicide nozzle 23, the cleaning tub 4, the drain outlet 55, the drain pipe 59, and the drain hose. Meanwhile, the user prepares a replacement bottle set (not shown) in which the bottles 6A and 6B used in the germicide preparation process are stored.

At the completion of the predetermined germicide draining process which is based on the germicide draining program, an instruction to start the germicide preparation process is displayed on the display part on the main operation panel 25 or the sub operation panel 13. At this point, the user starts the germicide preparation process.

Referring to FIGS. 8 to 11, the following will describe the steps of the germicide preparation process which is based on a germicide preparation program.

First, the user operates the germicide preparation button 13g provided on the sub operation panel 13 of the endoscope cleaning/disinfecting apparatus 1. Thus an instruction signal is outputted from the germicide preparation button 13g to the control unit 90, and the control unit 90 having received the instruction signal starts control based on the germicide preparation program stored in the program memory 93.

Figure 8:
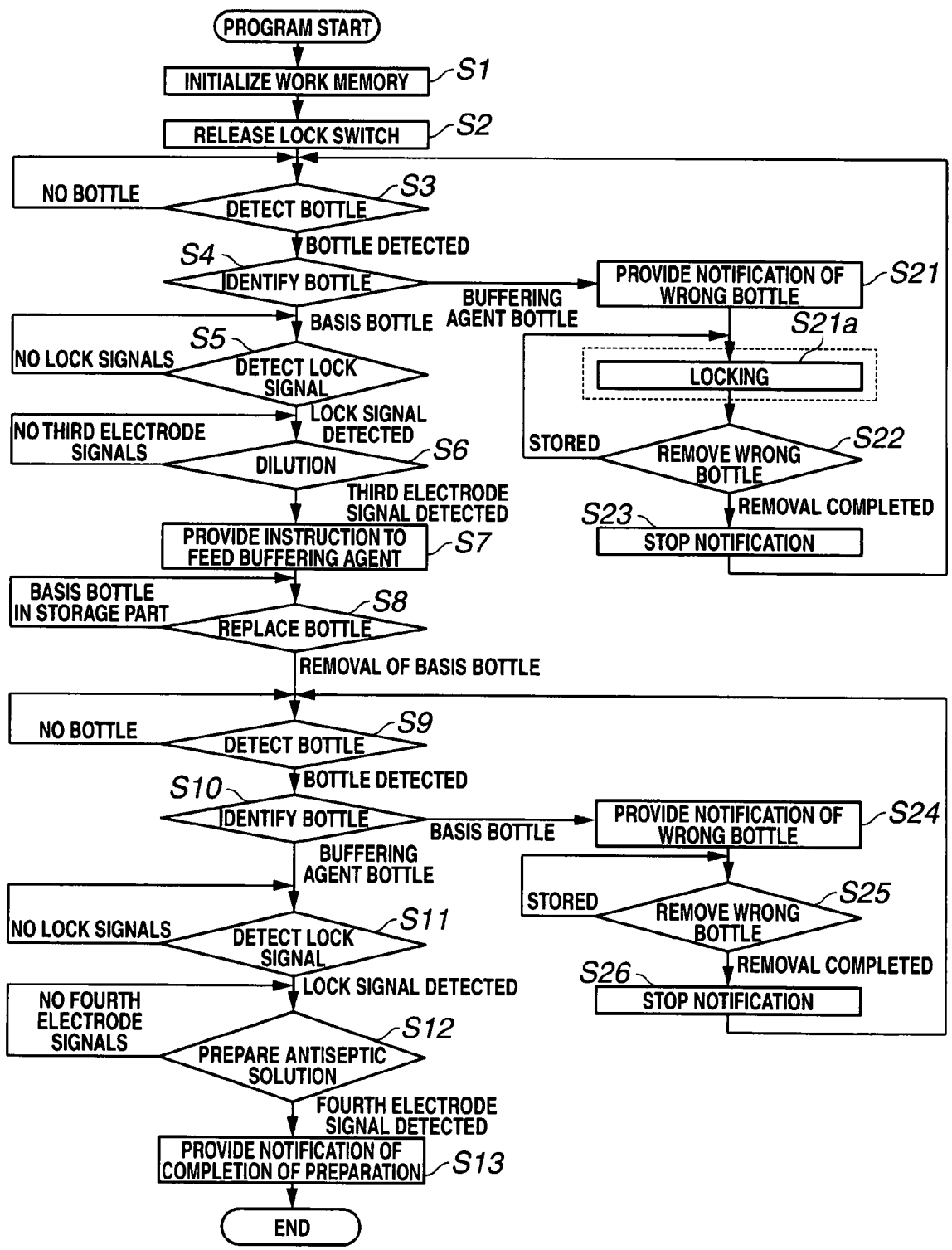

In other words, as indicated in step S1 of FIG. 8, the control unit 90 initializes the work memory 94. At this point, the empty buffering agent bottle 6B is stored in the storage part 120 of the germicide bottle tray 12 and the work memory 94 stores "the first detection portion 123=OFF, the second detection portion 124=OFF". Further, the lock switch 2a is in a lock state and the work memory 94 stores "the lock switch=OFF".

In step S2, the control unit 90 outputs a control signal for releasing the lock state of the lock switch 2a and releases the lock state of the lock switch 2a. Since the lock state of the lock switch 2a is released, the output of the lock signal from the lock switch 2a is stopped. At this point, the work memory 94 stores "the lock switch=OFF".

After that, the control unit 90 shifts to the bottle detection of step S3. The bottle detection is processing for confirming the presence or absence of a bottle in the storage part 120 and deciding whether the first detection portion 123 is turned on or not. When the first detection portion 123 switches from OFF to ON, the control unit 90 shifts to the bottle identification of step S4. In other words, the control unit 90 is in a standby state until the first detection portion 123 switches from OFF to ON.

During that time, the user who has operated the germicide preparation button 13g draws the germicide bottle tray 12 to the front of the apparatus body 2. Next, the user removes the empty buffering agent bottle 6B stored in the storage part 120 of the germicide bottle tray 12. Thus the work memory 94 stores "the first detection portion 123=OFF, the second detection portion 124=OFF".

After that, the user who has removed the empty buffering agent bottle 6B from the storage part 120 stores the basis bottle 6A in the storage part 120.

At this point, in the case where the user places the basis bottle 6A in the storage part 120 of the germicide bottle tray 12 as shown in FIG. 9, the first detection signal is outputted from the first detection portion 123 to the control unit 90. On the other hand, in the case where the user erroneously places the buffering agent bottle 6B in the storage part 120 of the germicide bottle tray 12 as shown in FIG. 10, the first detection signal from the first detection portion 123 and the second detection signal from the second detection portion 124 are outputted to the control unit 90.

In other words, when the user stores a bottle in the storage part 120, the first detection portion 123 switches from OFF to ON regardless of the kind of bottle. Thus the control unit shifts to step S4 and the work memory 94 stores "the first detection portion 123=ON".

In the bottle identification of step S4, it is decided whether the second detection portion 124 is turned on or off. When the second detection portion 124 is turned off, the control unit 90 shifts to step S5. When the second detection portion 124 is turned on, the control unit shifts to step S21.

To be specific, when the bottle is placed as shown in FIG. 9, the control unit 90 shifts to step S5. When the bottle is placed as shown in FIG. 10, the control unit 90 shifts to step S21. When the control unit 90 shifts to step S21, the work memory 94 stores "the second detection portion 124=ON".

Step S21 is notification of a wrong bottle. For example, the control unit 90 outputs to a buzzer (not shown) a warning signal for providing an instruction to start a warning beep, and emits the warning beep from the buzzer. After that, the control unit 90 shifts to the removal of a wrong bottle in step S22.

In the removal of a wrong bottle, it is decided whether the first detection portion 123 or the second detection portion 124 is turned off or the first detection portion 123 and the second detection portion 124 are turned off. In the present embodiment, the control unit 90 decides whether both of the first detection portion 123 and the second detection portion 124.are turned off. When the control unit 90 decides that the detection portions 123 and 124 are turned off, the control unit 90 stops the notification of step S23 and shifts to the bottle detection of step S3. In other words, the control unit 90 stands by until the first detection portion 123 and the second detection portion 124 both switch from ON to OFF. In step S23, the control unit 90 outputs a warning stop signal for instructing the buzzer to stop the warning beep.

The warning beep is emitted from the buzzer substantially concurrently with the placement of the bottle, and thus the user who has placed the buffering agent bottle 6B in the storage part 120 can immediately recognize that the bottle placed in the storage part 120 is not the basis bottle 6A. After that, the user removes the buffering agent bottle 6B from the storage part 120 and places the basis bottle 6A instead in the storage part 120.

During that time, the work memory 94 stores "the first detection portion 123=OFF, the second detection portion=OFF" and stores "the first detection portion 123=ON, the second detection portion=OFF" immediately thereafter.

While the control unit 90 shifts from step S21 to step S22, the control unit 90 may perform locking of step S21a. The locking of step S21a is processing for outputting a control signal which switches the lock switch 2a in the free state to the lock state. To be specific, in a state in which the buffering agent bottle 6B is stored in the storage part 120, the lock switch 2a is switched to the lock state, so that the germicide bottle tray 12 cannot be pressed back to the apparatus body 2. In this case, the lock state of the lock switch 2a is released after step S22.

Step S5 is the detection of the lock signal. In the detection of the lock signal, the control unit 90 detects the presence or absence of the lock signal outputted from the lock switch 2a. When the lock switch 2a switches from OFF to ON, the control unit 90 shifts to the dilution of step S6. In other words, the control unit 90 is in the standby state until the lock switch 2a switches from OFF to ON.

Figure 11:
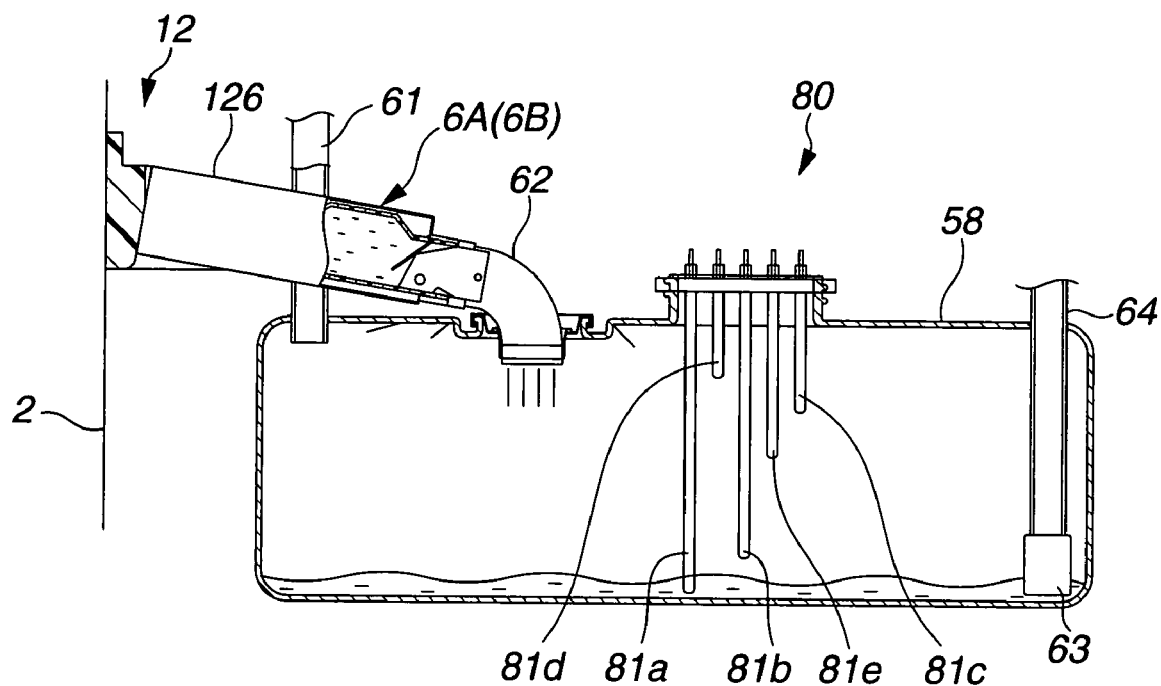

During that time, the user who has stored the basis bottle 6A in the storage part 120 presses the germicide bottle tray 12 back to the apparatus body 2. After that, when the germicide bottle tray 12 is stored in the apparatus body 2 in a predetermined state, the closed-portion opening portions 127 break through the thin portions 6i of the closed portions 6h and the chemical solution in the basis bottle 6A is supplied into the chemical solution tank 58 as shown in FIG. 11. At this point, the work memory 94 stores "the lock switch=ON".

Thereafter, the user makes preparations or the like for the supply of a chemical solution in the second bottle 6B into the chemical solution tank 58 while the chemical solution in the basis bottle 6A is drained into the chemical solution tank 58 and while the chemical solution is diluted with tap water.

The dilution of step S6 includes basis level detection and diluent level detection and is continued until a third electrode signal outputted from the third electrode sensor 81c is detected. When the third electrode signal is detected in step S6, the control unit 90 shifts to step S7.

The basis level detection is conducted until the chemical solution supplied from the basis bottle 6A into the chemical solution tank 58 reaches the second electrode sensor 81b and a second electrode signal is outputted from the second electrode sensor 81b. When the second electrode signal is detected, the control unit 90 shifts to the diluent level detection.

In the diluent level detection, the chemical solution supplied from the basis bottle 6A into the chemical solution tank 58 is diluted to a predetermined amount. The diluent level detection is conducted until tap water supplied into the chemical solution tank 58 reaches the third electrode sensor 81c and the third electrode signal is outputted from the third electrode sensor 81c under the control of the control unit 90.

To be specific, in the diluent detection, the control unit 90 performs control so that the water feed solenoid valve 15 is opened, the three-way solenoid valve 10 communicates with the feed nozzle 24, and the change-over valve 57 is opened so as to allow supplied water to pass the drain outlet 55 and flow into the chemical solution tank 58. Further, when detecting the third electrode signal outputted from the third electrode sensor 81c, the control unit 90 controls the water feed solenoid valve 15 and the change-over valve 57 such that the water feed solenoid valve 15 is closed and the change-over valve 57 is closed.

Step S7 is processing for providing an instruction to feed the buffering agent. For example, the control unit 90 performs control so that an instruction to feed the buffering agent is displayed on the display part on the main operation panel 25 or the sub operation panel 13 or the warning beep is emitted, and performs control so that the lock state of the lock switch 2a is released. After that, the control unit 90 shifts to the bottle replacement of step S8.

In the bottle replacement, it is decided whether the first detection portion 123 switches from ON to OFF. When the first detection portion 123 switches from ON to OFF, the control unit 90 shifts to the bottle detection of step S9.

When the lock state of the lock switch 2a is released, the output of the lock signal from the lock switch 2a is stopped. Thus the work memory 94 stores "the lock switch=OFF". Moreover, the control unit 90 is in the standby state until the first detection portion 123 switches from ON to OFF.

During that time, the user confirms the instruction displayed on the display part, and then draws the germicide bottle tray 12 to the front of the apparatus body 2. Next, the user removes the empty basis bottle 6A stored in the storage part 120 of the germicide bottle tray 12. Thus the work memory 94 stores "the first detection portion 123=OFF".

The bottle detection of step S9 is processing for detecting the presence or absence of the bottle. In other words, it is decided whether the first detection portion 123 is turned on or not. When the first detection portion 123 switches from OFF to ON, the control unit 90 shifts to the bottle identification of step S10. In other words, the control unit 90 is in the standby state until the first detection portion 123 switches from OFF to ON.

During that time, the user stores the buffering agent bottle 6B in the storage part 120. At this point, in the case where the user places the buffering agent bottle 6B in the storage part 120 as shown in FIG. 10, the first detection signal from the first detection portion 123 and the second detection signal from the second detection portion 124 are outputted to the control unit 90. On the other hand, in the case where the user erroneously places the basis bottle 6A in the storage part 120 as shown in FIG. 9, the first detection signal is outputted from the first detection portion 123 to the control unit 90.

In other words, when the user stores the bottle in the storage part 120, the first detection portion 123 switches from OFF to ON regardless of the kind of bottle. At this point, the control unit shifts to step S10 and the work memory 94 stores "the first detection portion 123=ON".

The bottle identification of step S10 is processing for deciding whether the second detection portion 124 is turned on or off. When the second detection portion 124 is turned on, the control unit 90 shifts to step S11. When the second detection portion 124 is turned off, the control unit 90 shifts to step S24. In other words, when the bottle is placed as shown in FIG. 10, the control unit 90 shifts to step S11 and the work memory 94 stores "the second detection portion 124=ON". Meanwhile, when the bottle is placed as shown in FIG. 9, the control unit 90 shifts to step S24.

Step S11 is the detection of the lock signal. The control unit 90 detects the presence or absence of the lock signal outputted from the lock switch 2a. When the lock switch 2a switches from OFF to ON, the control unit 90 shifts to the preparation of the germicide in step S12. In other words, the control unit 90 is in a standby state until the lock switch 2a switches from OFF to ON.

During that time, the user who has stored the buffering agent bottle 6B in the storage part 120 presses the germicide bottle tray 12 back to the apparatus body 2. When the germicide bottle tray 12 is stored in the apparatus body 2 in a predetermined state, the closed-portion opening portions 127 break through the thin portions 6i of the closed portions 6h and the chemical solution in the buffering agent bottle 6B is supplied into the chemical solution tank 58 as shown in FIG. 11. At this point, the work memory 94 stores "the lock switch=ON".

After that, the user stands by until the completion of the preparation of the germicide is displayed on, for example, the display part on the main operation panel 25 or the sub operation panel 13.

The preparation of the germicide in step S12 is continued until a fourth electrode signal outputted from the fourth electrode sensor 81d is detected. When the fourth electrode signal is detected in step S12, the control unit 90 shifts to step S13.

Step S13 is notification of the completion of preparation. In order to notify the user of the completion of the preparation of the germicide, the control unit 90 performs control, for example, so that the completion of the preparation of the germicide is displayed on the display part on the main operation panel 25 or the sub operation panel 13. Thus the germicide preparation process based on the germicide preparation program is completed.

Step S24 is notification of a wrong bottle and similar to step S21. In this step, the control unit 90 emits a warning beep from the buzzer. After that, the control unit 90 shifts to the removal of a wrong bottle in step S25.

In the removal of a wrong bottle, the control unit 90 decides whether both of the first detection portion 123 and the second detection portion 124 are turned off or not as in step S22. When the control unit 90 decides that the detection portions 123 and 124 are turned off, the control unit 90 stops the notification of step S26 and shifts to the bottle detection of step S9.

The warning beep is emitted from the buzzer substantially concurrently with the placement of the bottle, and thus the user who has placed the bottle in the storage part 120 can immediately recognize that the bottle placed in the storage part 120 is not the buffering agent bottle 6B. After that, the user removes the basis bottle 6A from the storage part 120 and places the buffering agent bottle 6B instead in the storage part 120.

During that time, the work memory 94 stores "the first detection portion 123=OFF, the second detection portion OFF" and stores "the first detection portion 123=ON, the second detection portion ON" immediately thereafter.

As described above, bases and buffering agents of various germicides are stored in the bottles 6A and 6B which are formed into bottles, and the bottle detection switch 123 and the bottle identification switch 124 are provided in the storage part 120 of the germicide bottle tray 12 for storing the bottles 6A and 6B. Further, the germicide preparation program is provided for the germicide bottle tray 12 which includes the bottles 6A and 6B and the switches 123 and 124. Thus cleaning and disinfecting can be performed in a similar manner to a dedicated type even with a plurality of different germicides, without the need to considerably change the design of the cleaning/disinfecting apparatus body 2 of the endoscope cleaning/disinfecting apparatus 1.

In the present embodiment, the bottle detection switches 123 and 124 are described as mechanical switches which can be protruded and depressed. Thus in the case where the bottles 70A and 70B of FIGS. 14 and 15 are configured as the bottle body 70 and stored in the storage part 120 of the present embodiment, the bottle detection switches 123 and 124 are, for example, noncontacting electric switches such as a photoelectric switch. It is therefore possible to store the bottles 70A and 70B in the storage part 120 without forming a relief portion on the bottles 70A and 70B to relieve the bottle detection switches 123 and 124, that is, without changing the designs of the bottles 70A and 70B.

The steps of the germicide preparation process are not limited to the steps based on the foregoing germicide preparation program but may be based on another germicide preparation program.

Figure 12:
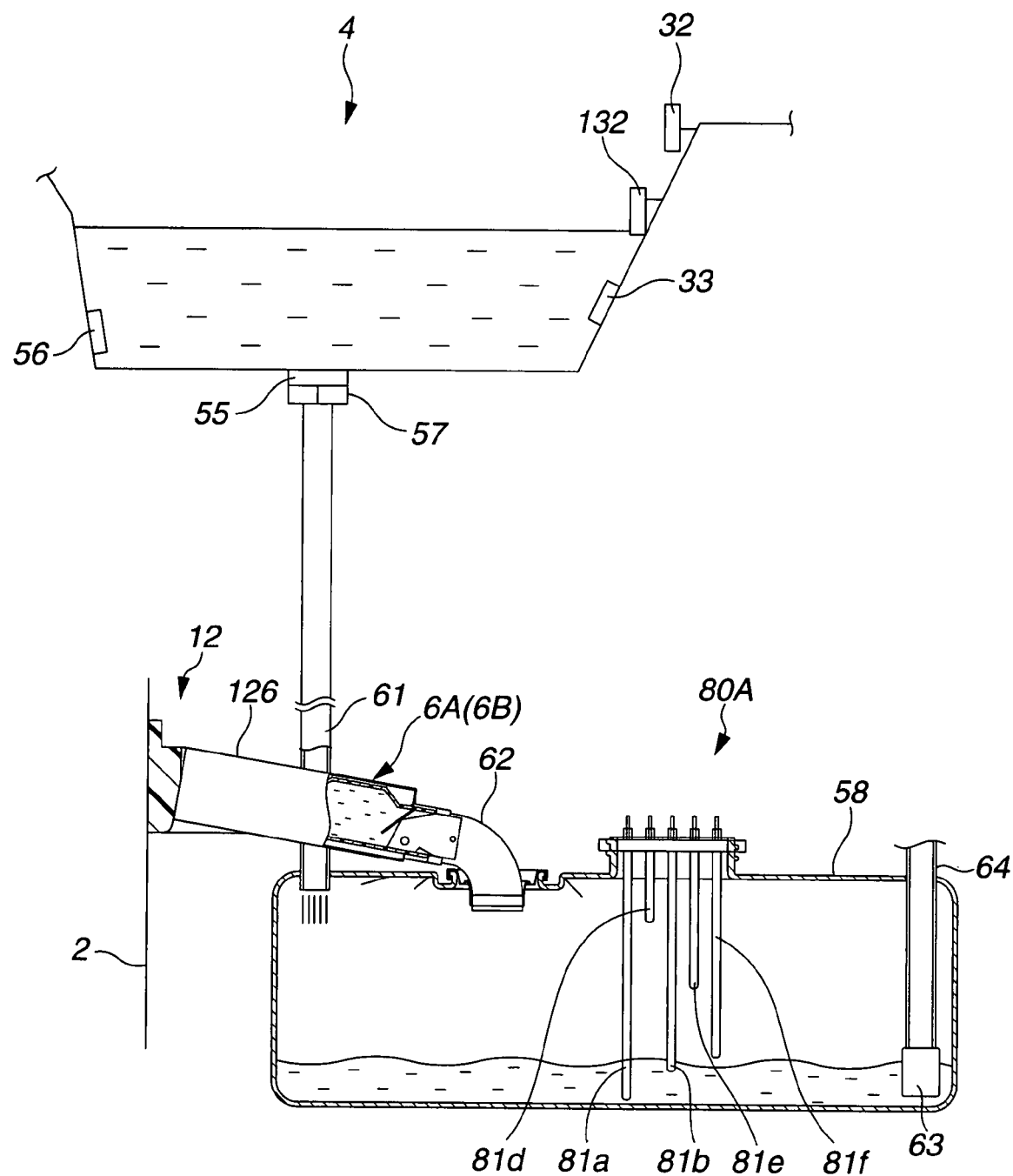
FIGS. 12 and 13 illustrate the steps of a germicide preparation process based on another germicide preparation program.
Figure 13:
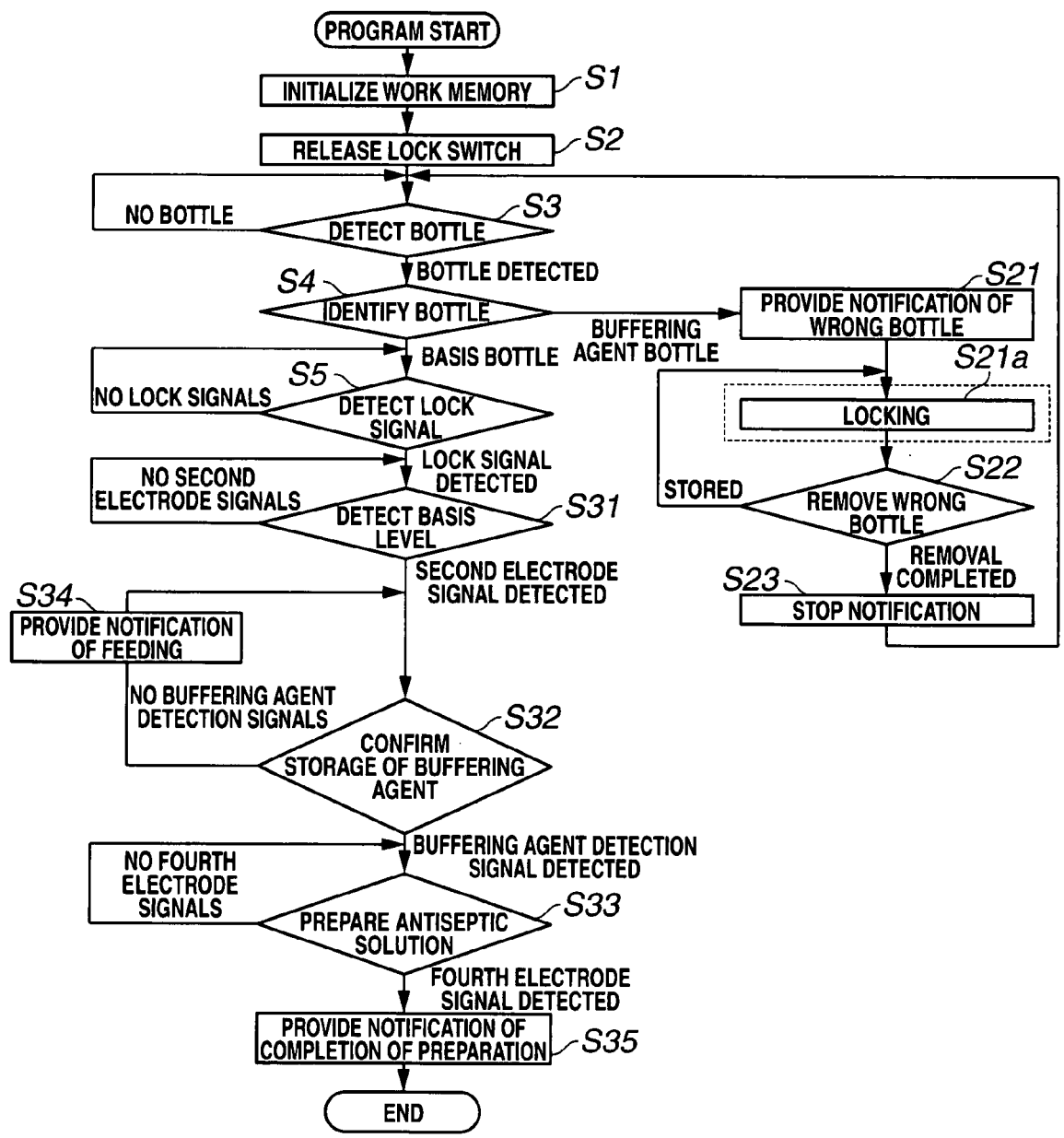

FIGS. 12 and 13 illustrate the steps of a germicide preparation process based on another germicide preparation program. FIG. 12 illustrates a fluid volume detection unit and FIG. 13 is a flowchart for explaining the another germicide preparation program.

The germicide preparation program of FIG. 13 is similar to that of the foregoing embodiment until step S5. For convenience, the germicide preparation program of the present embodiment will be referred to as a second germicide preparation program as distinguished from the germicide preparation program of the foregoing embodiment. Further, the germicide preparation program of the foregoing embodiment will be referred to as a first germicide preparation program when necessary as distinguished from the second germicide preparation program.

In the present embodiment, as shown in FIG. 12, a cleaning tub 4 includes a buffering agent volume detection sensor 132. The buffering agent volume detection sensor 132 is a sensor for detecting a volume of a buffering agent fed into a cleaning tub 4. When the level of the buffering agent reaches the buffering agent volume detection sensor 132, the buffering agent volume detection sensor 132 outputs a buffering agent detection signal to a control unit 90.

Meanwhile, a fluid volume detection unit 80A includes a plurality of electrode sensors 81a, 81b, 81d, 81e and 81f having different lengths. In the present embodiment, a sixth electrode sensor 81f is provided instead of the third electrode sensor 81c.

The first electrode sensor 81a is a ground electrode. The second electrode sensor 81b is a basis level detection sensor and an electrode for detecting the volume of a chemical solution supplied from a basis bottle 6A to a chemical solution tank 58. The fourth electrode sensor 81d is a germicide level detection sensor and an electrode for detecting the volume of a germicide prepared by mixing the chemical solution of the basis bottle 6A, water serving as a diluent, and a chemical solution stored in the cleaning tub 4 and supplied therefrom. The fifth electrode sensor 81e is an electrode for detecting the minimum volume required for supplying a germicide into the cleaning tub 4 in a cleaning/disinfecting state. The sixth electrode sensor 81f is a mixed solution level detection sensor and an electrode for detecting the volume of a two-component mixed solution of a basis supplied from the basis bottle 6A and a buffering agent stored in the cleaning tub 4 and supplied therefrom.

First, the user operates a germicide preparation button 13g provided on a sub operation panel 13 of an endoscope cleaning/disinfecting apparatus 1. Thus an instruction signal is outputted from the germicide preparation button 13g to the control unit 90, and the control unit 90 having received the instruction signal starts control based on the second germicide preparation program stored in a program memory 93.

In other words, as indicated in step S1 of FIG. 13, the control unit 90 initializes a work memory 94. At this point, the empty basis bottle 6A is stored in a storage part 120 of a germicide bottle tray 12 and the work memory 94 stores "a first detection portion 123 =OFF, a second detection portion 124=OFF". A lock switch 2a is in a lock state and the work memory 94 stores "the lock switch=OFF".

In step S2, the control unit 90 outputs a control signal for releasing the lock state of the lock switch 2a and releases the lock state of the lock switch 2a. Since the lock state of the lock switch 2a is released, the output of the lock signal from the lock switch 2a is stopped. At this point, the work memory 94 stores "lock switch=OFF".

After that, the control unit 90 shifts to the bottle detection of step S3. The bottle detection is processing for confirming the presence or absence of the bottle in the storage part 120, and deciding whether the first detection portion 123 is turned on or not. When the first detection portion 123 switches from OFF to ON, the control unit 90 shifts to the bottle identification of step S4. In other words, the control unit 90 is in a standby state until the first detection portion 123 switches from OFF to ON.

During that time, the user who has operated the germicide preparation button 13g draws the germicide bottle tray 12 to the front of the apparatus body 2. Next, the user removes the empty basis bottle 6A stored in the storage part 120 of the germicide bottle tray 12. Thus the work memory 94 stores "the first detection portion 123=OFF, the second detection portion 124=OFF".

After that, the user who has removed the empty basis bottle 6A from the storage part 120 stores the basis bottle 6A in which a chemical solution is stored in the storage part 120.

At this point, in the case where the user places the basis bottle 6A in the storage part 120 of the germicide bottle tray 12 as shown in FIG. 9, a first detection signal is outputted from the first detection portion 123 to the control unit 90. On the other hand, in the case where the user erroneously places a bottle different from the basis bottle 6A in the storage part 120, a different detection signal is outputted to the control unit 90. For example, the first detection signal from the first detection portion 123 and a second detection signal from the second detection portion 124 are outputted to the control unit 90.

In other words, when the user stores a bottle in the storage part 120, the first detection portion 123 switches from OFF to ON regardless of the kind of bottle. Thus the control unit shifts to step S4 and the work memory 94 stores "the first detection portion 123=ON ".

In the bottle identification of step S4, it is decided whether the second detection portion 124 is turned on or off. When the second detection portion 124 is turned off, the control unit 90 shifts to step S5. When the second detection portion 124 is turned on, the control unit shifts to step S21.

To be specific, when the bottle is placed as shown in FIG. 9, the control unit 90 shifts to step S5. When the bottle is placed as shown in FIG. 10, the control unit 90 shifts to step S21. When the control unit 90 shifts to step S21, the work memory 94 stores "the second detection portion 124=ON ".

Step S21 is notification of a wrong bottle. For example, the control unit 90 outputs to a buzzer (not shown) a warning signal for providing an instruction to start a warning beep, and emits the warning beep from the buzzer. After that, the control unit 90 shifts to removal of a wrong bottle in step S22.

In the removal of a wrong bottle, the control unit 90 decides whether the first detection portion 123 and the second detection portion 124 are both turned off or not. When the control unit 90 decides that the detection portions 123 and 124 are turned off, the control unit 90 stops the notification of step S23 and shifts to the bottle detection of step S3.

The warning beep is emitted from the buzzer substantially concurrently with the placement of the bottle, and thus the user who has placed a bottle different from the basis bottle 6A in the storage part 120 can immediately recognize that the bottle placed in the storage part 120 is not the basis bottle 6A. After that, the user removes the different bottle from the storage part 120 and places the basis bottle 6A instead in the storage part 120.

During that time, the work memory 94 stores "the first detection portion 123=OFF, the second detection portion OFF " and stores "the first detection portion 123=ON, the second detection portion OFF " immediately thereafter.

While the control unit 90 shifts from step S21 to step S22, the control unit 90 may perform locking of step S21a. The locking of step S21a is processing for outputting a control signal which switches the lock switch 2a in a free state to the lock state. To be specific, in a state in which the buffering agent bottle 6B is stored in the storage part 120, the lock switch 2a is switched to the lock state, so that the germicide bottle tray 12 cannot be pressed back to the apparatus body 2. In this case, the lock state of the lock switch 2a is released after step S22.

Step S5 is the detection of a lock signal. In the detection of the lock signal, the control unit 90 detects the presence or absence of the lock signal outputted from the lock switch 2a. When the lock switch 2a switches from OFF to ON, the control unit 90 shifts to the basis level detection of step S31. In other words, the control unit 90 is in a standby state until the lock switch 2a switches from OFF to ON.

During that time, the user who has stored the basis bottle 6A in the storage part 120 presses the germicide bottle tray 12 back to the apparatus body 2. Further, when the germicide bottle tray 12 is stored in the apparatus body 2 in a predetermined state, closed-portion opening portions 127 break through thin portions 6i of closed portions 6h and the chemical solution in the basis bottle 6A is supplied into the chemical solution tank 58 as shown in FIG. 1. At this point, the work memory 94 stores "the lock switch=ON ".

Thereafter, while the chemical solution in the basis bottle 6A is drained into the chemical solution tank 58, the user pours into the cleaning tub the buffering agent which has a predetermined volume and is stored in the buffering agent bottle 6B or another container. After that, the user stands by until the completion of the preparation of the germicide is displayed on, for example, a display part on a main operation panel 25 or a sub operation panel 13.

The basis level detection of step S31 is conducted until the chemical solution supplied from the basis bottle 6A into the chemical solution tank 58 reaches the second electrode sensor 81b and a second electrode signal is outputted from the second electrode sensor 81b. When the second electrode signal is detected, the control unit 90 shifts to confirmation of the storage of the buffering agent in step S32.

In the confirmation of the storage of the buffering agent in step S32, it is confirmed whether or not the buffering agent detection signal indicating a storage state is outputted from the buffering agent volume detection sensor 132 to the control unit 90. When the buffering agent detection signal is confirmed, the control unit 90 shifts to the germicide preparation of step S33. When the buffering agent detection signal is not confirmed, the control unit 90 shifts to notification of feeding in step S34. Step S34 urges the user to feed the buffering agent into the cleaning tub 4.

In the notification of feeding in step S34, the control unit 90 outputs, for example, a warning signal to a buzzer (not shown) and emits the warning beep from the buzzer. The warning signal provides an instruction to start the warning beep. Further, the control unit 90 performs control so that an instruction to feed the buffering agent into the tank is displayed on the display part on the main operation panel 25 or the sub operation panel 13, and then the control unit 90 shifts to step S32.

The germicide preparation of step S33 includes mixed solution level detection and germicide level detection and is continued until a fourth electrode signal outputted from the fourth electrode sensor 81d is detected. When the fourth electrode signal is detected in step S33, the control unit 90 shifts to step S35.

The mixed solution level detection is processing for detecting the level of a two-component mixed solution obtained by mixing the buffering agent in the cleaning tub 4 with the chemical agent supplied from the basis bottle 6A into the chemical solution tank 58. In the mixed solution level detection, the buffering agent in the cleaning tub 4 is supplied into the chemical solution tank 58 as shown in FIG. 12 until a sixth electrode signal is outputted from the sixth electrode sensor 81f under the control of the control unit 90. To be specific, the control unit 90 performs control so that a change-over valve 57 is opened so as to feed the buffering agent in the cleaning tub 4 into the chemical solution tank 58 through a drain outlet 55. Next, when detecting the sixth electrode signal outputted from the sixth electrode sensor 81f, the control unit 90 shifts to the germicide level detection.

The germicide detection of the present embodiment is processing for detecting the level of the germicide which is a mixed solution of a two-component mixed solution of the chemical solution of the basis bottle 6A and the buffering agent and water serving as a diluent. The chemical solution of the basis bottle 6A and the buffering agent have been supplied into the chemical solution tank 58. In the detection of the germicide, tap water is supplied into the chemical solution tank 58 until the fourth electrode signal is outputted from the fourth electrode sensor 81d under the control of the control unit 90. To be specific, the control unit 90 performs control so that a water feed solenoid valve 15 is opened and a three-way solenoid valve 10 communicates with the feed nozzle 24. Further, when detecting the fourth electrode signal outputted from the fourth electrode sensor 81d, the control unit 90 performs control so that the water feed solenoid valve 15 is closed and the change-over valve 57 is closed. After that, the control unit 90 shifts to step S35.

Step S35 is notification of the completion of preparation. In order to notify the user of the completion of the preparation of the germicide, the control unit 90 performs control so that the completion of the preparation of the germicide is displayed on, for example, the display part on the main operation panel 25 or the sub operation panel 13. Further, the control unit 90 outputs to a buzzer (not shown) a warning beep output signal for providing an instruction to start a warning beep, and emits the warning beep from the buzzer. Thus the germicide preparation process based on the second germicide preparation program is completed.

As described above, since the buffering agent volume detection sensor 132 is provided in the cleaning tub 4, the basis bottle 6A for storing the basis and the bottle for storing the buffering agent are formed with different shapes and it is possible to prevent the bottle for storing the buffering agent from being stored in the storage part 120 of the germicide bottle tray 12.

Further, since a predetermined volume of the buffering agent is fed into the cleaning tub 4 while the chemical solution of the basis bottle 6A is supplied into the chemical solution tank 58, the user can thereafter perform another operation away from the endoscope cleaning/disinfecting apparatus 1.

Other operation/working effects are similar to those of the steps based on the first germicide preparation program.

The present invention is not limited to the foregoing embodiments and thus various modifications may be made without departing from the gist of the invention.

What is claimed is:

1. An endoscope cleaning/disinfecting apparatus, comprising:
   a cleaning tub disposed on a body of the disinfecting apparatus and stores an endoscope;
   a chemical solution tank disposed in the body of the disinfecting apparatus and configured to store a germicide obtained by mixing a basis, a buffering agent, and water as a diluent;
   a chemical solution collection pipe connecting the cleaning tub and the chemical solution tank;
   a chemical solution pipe disposed between the chemical solution tank and the cleaning tub, the chemical solution pipe supplying the germicide in the chemical solution tank to the cleaning tub;
   a chemical solution supply pipe having a first end communicating with the chemical solution tank;
   a mouth placement part provided on a second end of the chemical solution supply pipe;
   a feed pipe supplying the water into the cleaning tub and the chemical solution tank;
   a germicide bottle tray including:
     a storage part which can be drawn from the body of the cleaning/disinfecting apparatus and stores a bottle body for storing the basis and a second bottle body for storing the buffering agent, alternatively; and
     a detection portion outputting a detection signal when the bottle body is stored in the storage part, the detection portion having a first detection portion adapted for detecting whether the bottle body is stored in the storage part, and a second detection portion adapted to distinguish whether the bottle body stored in the storage part is the first bottle body or the second bottle body, the germicide bottle tray disposed for guiding a mouth of the bottle body stored in the storage part, by pressing back the germicide bottle tray, to the mouth placement part; and a control unit adapted for performing control, based on the detection signal outputted from the detection portion, so that the germicide is prepared by mixing the basis, the buffering agent, and the diluent.

2. The endoscope cleaning/disinfecting apparatus according to claim 1, further comprising a tray operation switching portion for switching the germicide bottle tray between a drawable state and an immovable state.

3. The endoscope cleaning/disinfecting apparatus according to claim 1, wherein the control unit controls at least one of the tray operation switching portion, a water feed solenoid valve of the feed pipe, a three-way solenoid valve, and a change-over valve of the chemical solution collection pipe based on a germicide preparation program for preparing the germicide by mixing the basis, the buffering agent, and the diluent.

4. The endoscope cleaning/disinfecting apparatus according to claim 1, wherein when it is detected based on a detection result of the second detection portion that a wrong bottle body is stored in the storage part, the control unit controls the tray operation switching portion in a lock state based on a germicide preparation program for preparing the germicide by mixing the basis, the buffering agent, and the diluent.

5. The endoscope cleaning/disinfecting apparatus according to claim 1, wherein in a configuration where the first bottle body and the second bottle body can be each stored in the storage part, at least one of the first bottle body and the second bottle body includes an identification portion for identifying a type of the bottle body.

6. The endoscope cleaning/disinfecting apparatus according to claim 1, wherein in a configuration where the first bottle body and the second bottle body can be each stored in the storage part, at least one of the first bottle body and the second bottle body includes an identification portion detectable by the second detection portion.

7. The endoscope cleaning/disinfecting apparatus according to claim 5, further comprising a fluid volume detection unit provided in the chemical solution tank, the fluid volume detection unit at least including:
a basis level detection sensor for detecting a volume when the basis in the first bottle is fully supplied into the tank;
a diluent level detection sensor for detecting, when mixing the basis with the diluent for diluting the basis, a volume of the basis diluted with the diluent; and
a germicide level detection sensor for detecting, when mixing the diluted basis with the buffering agent in the second bottle, a volume of the germicide which is a mixed solution of the basis, the diluent, and the buffering agent.

8. The endoscope cleaning/disinfecting apparatus according to claim 6, further comprising a fluid volume detection unit provided in the chemical solution tank, the fluid volume detection unit at least including:
a basis level detection sensor for detecting a volume when the basis in the first bottle is fully supplied into the tank;
a diluent level detection sensor for detecting, when mixing the basis with the diluent for diluting the basis, a volume of the basis diluted with the diluent; and
a germicide level detection sensor for detecting, when mixing the diluted basis with the buffering agent in the second bottle, a volume of the germicide which is a mixed solution of the basis, the diluent, and the buffering agent.

9. The endoscope cleaning/disinfecting apparatus according to claim 1, further comprising a fluid volume detection unit provided in the chemical solution tank, the fluid volume detection unit at least including:
a basis level detection sensor for detecting a volume when the basis in the first bottle is fully supplied into the tank;
a mixed solution level detection sensor for detecting, when mixing the basis with the buffering agent in the second bottle, a volume of a two-component mixed solution prepared by mixing the basis and the buffering agent; and
a germicide level detection sensor for detecting, when mixing the two-component mixed solution with the diluent for diluting the two-component mixed solution, a volume of the germicide which is a mixed solution of the basis, the buffering agent, and the diluent.

10. The endoscope cleaning/disinfecting apparatus according to claim 2, further comprising a fluid volume detection unit provided in the chemical solution tank, the fluid volume detection unit at least including:
a basis level detection sensor for detecting a volume when the basis in the first bottle is fully supplied into the tank;
a mixed solution level detection sensor for detecting, when mixing the basis with the buffering agent in the second bottle, a volume of a two-component mixed solution prepared by mixing the basis and the buffering agent; and
a germicide level detection sensor for detecting, when mixing the two-component mixed solution with the diluent for diluting the two-component mixed solution, a volume of the germicide which is a mixed solution of the basis, the buffering agent, and the diluent.

11. An endoscope cleaning/disinfecting apparatus, comprising:
a chemical solution tank storing a germicide obtained by mixing a basis, a buffering agent, and tap water as a diluent;
a cleaning tub configured to clean an endoscope stored therein with the germicide;
a chemical solution pipe disposed between the chemical solution tank and the cleaning tub, the chemical solution pipe supplying the germicide of the chemical solution tank into the cleaning tub;
a chemical solution supply pipe having a first end in communication with the chemical solution tank;
a mouth placement part provided on a second end of the chemical solution supply pipe;
a feed pipe supplying tap water into the cleaning tub and the chemical solution tank;
a chemical solution collection pipe connecting the cleaning tub and the chemical solution tank;
a germicide bottle tray including a storage part which alternatively stores either a first bottle body storing the basis, or a second bottle body storing the buffering agent, and which comprises a first detection portion adapted for detecting whether the bottle body is stored in the storage part and a second detection portion adapted for detecting whether the bottle body stored in the storage part is the first bottle body based on the shape of the bottle body, the germicide bottle tray disposed for guiding a mouth of the bottle body stored in the storage part to the mouth placement part; and
a control unit adapted for performing control, based on detection signals outputted from the first detection portion and the second detection portion and a germicide preparation program, so that the germicide is prepared by mixing the basis, the buffering agent, and the tap water.

12. The endoscope cleaning/disinfecting apparatus according to claim 11, wherein after having stored the first bottle body in the storage part and having supplied the basis into the chemical solution tank, the first bottle body is taken out of the storage part, the second bottle body is stored in the storage part in place of the first bottle body, and the buffering agent is supplied into the chemical solution tank.

13. The endoscope cleaning/disinfecting apparatus according to claim 12, wherein if the second bottle body is stored in the storage part prior to the first bottle body, the control unit generates a warming based on the output signal of the second detection portion.

14. An endoscope cleaning/disinfecting system, comprising:
   a first bottle body containing a basis, the first bottle body having a first triggering structure and a second triggering structure;
   a second bottle containing a buffering agent, the second bottle body having a first triggering structure; and
   a cleaning/disinfecting apparatus having a germicide bottle tray, the germicide bottle tray comprising:
   a bottle storage part configured to be drawn out from the cleaning/disinfecting apparatus, the bottle storage part being dimensioned for singly receiving the first bottle body and the second bottle body,
   a detection part including:
      a first detector triggered by the first triggering structure of the first bottle body or second bottle body, and
      a second detector triggered by the second triggering structure of the first bottle body,
      wherein the detection part is configured to generate a detection signal in response to detection states of the first detector and the second detector, and
   a control unit configured to control preparation of the germicide from the basis, the buffering agent, and a diluent in response to the detection signal received from the detection portion.

* * * * *